United States Patent
Gigliotti et al.

(10) Patent No.: US 9,512,189 B2
(45) Date of Patent: Dec. 6, 2016

(54) OPTIMIZED ANTIGENS OF PNEUMOCYSTIS AND USE THEREOF

(75) Inventors: Francis Gigliotti, Pittsford, NY (US); Terry W Wright, West Henrietta, NY (US); Constantine G. Haidaris, Rochester, NY (US); Patricia J. Simpson-Haidaris, Rochester, NY (US)

(73) Assignee: University of Rochester, Rochester, NY (US)

(*) Notice: Subject to any disclaimer, the term of this patent is extended or adjusted under 35 U.S.C. 154(b) by 130 days.

(21) Appl. No.: 14/237,133

(22) PCT Filed: Aug. 6, 2012

(86) PCT No.: PCT/US2012/049758
§ 371 (c)(1),
(2), (4) Date: May 28, 2014

(87) PCT Pub. No.: WO2013/020133
PCT Pub. Date: Feb. 7, 2013

(65) Prior Publication Data
US 2014/0271656 A1     Sep. 18, 2014

Related U.S. Application Data

(60) Provisional application No. 61/515,133, filed on Aug. 4, 2011.

(51) Int. Cl.
| | |
|---|---|
| *C07K 14/44* | (2006.01) |
| *A61K 39/00* | (2006.01) |
| *C07K 16/20* | (2006.01) |
| *C12N 9/02* | (2006.01) |

(52) U.S. Cl.
CPC ............ *C07K 14/44* (2013.01); *A61K 39/00* (2013.01); *A61K 39/0002* (2013.01); *C07K 16/20* (2013.01); *C12N 9/0051* (2013.01); *A61K 2039/55566* (2013.01)

(58) Field of Classification Search
None
See application file for complete search history.

(56) References Cited

U.S. PATENT DOCUMENTS

| | | |
|---|---|---|
| 7,815,918 B2 | 10/2010 | Gigliotti et al. |
| 2008/0171053 A1* | 7/2008 | Gigliotti ............... C07K 14/37 424/165.1 |

FOREIGN PATENT DOCUMENTS

WO    2005/065382 A2    7/2005

OTHER PUBLICATIONS

Wells et al., 'Active Immunization Against Pneumocystis carinii with a Recombinant *P. carinii* Antigen,' American Society for Microbiology 74(4):2446-2448 (2006).
Beck et al., 'Pneumocystis Workshop: 10th Anniversary Summary,' American Society for Microbiology 8(4):446-460 (2009).
International Search Report and Written Opinion for PCT/US2012/049758, filed Aug. 6, 2012 (mailed Mar. 25, 2013).

* cited by examiner

*Primary Examiner* — Gary Nickol
*Assistant Examiner* — Khatol Shahnan Shah
(74) *Attorney, Agent, or Firm* — LeClairRyan, a Professional Corporation

(57) ABSTRACT

Immunologically active agents are described, including isolated *Pneumocystis* A 12 protein or polypeptides; immunogenic conjugates containing *Pneumocystis* A 12 protein or polypeptide of the present invention; antibodies recognizing the *Pneumocystis* A 12 protein or polypeptide or the immunogenic conjugates of the present invention; and nucleic acid molecules that encode the *Pneumocystis* A 12 protein or polypeptide of the present invention, as well as DNA constructs, expression vectors, and host cells that contain the nucleic acid molecules. Disclosed uses of the antibodies, immunogenic conjugates, and DNA constructs include inducing passive or active immunity to treat or prevent pathogen infections, particularly by a *Pneumocystis* organism, in a subject.

5 Claims, 8 Drawing Sheets

| Relative Adaptivity | Codon | Amino Acid | N-terminal Instances | C-terminal Instances |
|---|---|---|---|---|
| ≤ 30% | | | | |
| | AGG | Arginine | 10 | 0 |
| | CGA | Arginine | 3 | 7 |
| | CTA | Leucine | 10 | 2 |
| | CTC | Leucine | 6 | 2 |
| | | TOTAL | 29 | 11 |
| > 30% but ≤ 50% | | | | |
| | AAG | Lysine | 8 | 9 |
| | AGA | Arginine | 11 | 10 |
| | ATA | Isoleucine | 9 | 18 |
| | CCC | Proline | 2 | 1 |
| | CGG | Arginine | 1 | 1 |
| | CTT | Leucine | 12 | 5 |
| | TTA | Leucine | 27 | 10 |
| | TTG | Leucine | 9 | 6 |
| | | TOTAL | 79 | 60 |

```
                    ↓
MFFLRIIFIF  IFLKISYAEN  TDKLSDFEKK  YPELYQANPH  ALKLEALKSG
FSGKSVKKGL  GVFHIGNLGH  YRDHKPVILH  VIMGLTVGLA  ECRGTLAERC
KVIKALGNPI  TQYCNKPYDT  CQDYFDARNY  LLPMKDQLKN  PHAHHDACRT
ILLNCLFFKH  RNYITSDCVP  LVALCYLRVR  QNFVEAIMTE  ALRGEINTKG
AAAAMKKVCE  KIGHESPDLL  HLCFKTTVLE  KPKRSNKQYI  EDVKSRIRTV
STGNCRQVLE  ECYFNVLDYP  DIYQSCRNFR  RFCSEIGVVY  TPVDSTFDLF
QKPLSAEKLL  IDTSSKISED  LGLGFSKYVQ  KKSSNLEIAA  YLVNKTWVYD
NDCRNKLKEL  CLHIASLPLT  KQLCTLAHDR  NSKLCRDFYN  SIGTECYSLY
YEFKNVGLLY  NYTYRLSRDQ  CSKYVERCLF  LREQYAYWNS  LDTCANVFSS
CYKEDMDFSA  KLDLLNRIKD  KIVVPKGNTR  YFVELLCKSY  IVAECSASDL
MFKSYALMEA  CLHPERICRE  LKNHFSEESR  KLENKLRSIL  KPTYYECKDL
GQKCNSGFYF  DGDIEAQCNH  FKKRCQDKQE  RLKLINHIVD  SSALYLANEV
QCRTYFDSFC  GANVQEFKQ   ICNKGANGIC  PDIIDDSKEH  CAHLINHLTS
LGISSSSASL  PLDYCDSAIN  YCNSLSKFCT  ESKRQCDSVI  SFCTSESKKT
DEYGSFIDQY  PAAAANATKC  KVTLKELCQD  SSKKDSYSTL  CAYNKDGYTE
ICKNLRNFIE  KACENLRIHL  HTYDTNSLNT  NKGSAQDRCT  YIRNLYFKFK
NICLLVDPFY  DLSPIITQEC  KTNISEPALP  DKDPQPTSSP  QPKPRPRPRP
QPQPHPHPKP  QPQPTPEPQP  QPAPEPRPQP  TSKPRPQPTS  KPRPQPTPEP
RPLPVPGPGP  LPVPGPRPQP  QPQPQPQPQP  QPQPQPQPQP  QPQPQPQPQP
QPKPQPPSQS  TSESASQSKP  KPTTQTKPSP  RPHPKPVPKP  SSIDTGPSKS
DSSFIFTVTK  TITKISETEK  PSTKPSVKPT  STKTTSKPST  KPSTKPSVKP
ANHSTKTTSE  SEKPTLEEVP  ETKGNGVRVI  GFEGLQLLSM  IVAIIIGIWI
M
```

FIG. 3

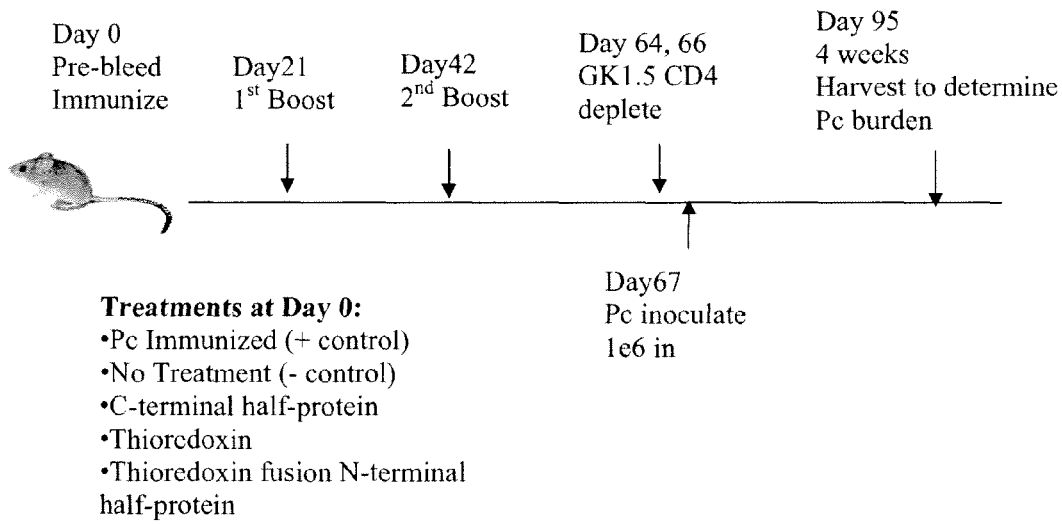

Treatments at Day 0:
- Pc Immunized (+ control)
- No Treatment (- control)
- C-terminal half-protein
- Thioredoxin
- Thioredoxin fusion N-terminal half-protein

| Exp | thio-c1 | thio | Pc | none |
|---|---|---|---|---|
| 410 | 0/5 | 3/3 | ND | 3/3 |
| 510 | 0/10 | 2/3 | 0/3 | 3/3 |
| 511 | 0/7 | 8/8 | 0/3 | 3/3 |
| 611 | 2/5 | 4/4 | 0/3 | ND |
| Total | 2/27 | 17/18 | 0/9 | 9/9 |

MFFLRIIFIFIFLKISYA[Forward1]ENTDKLSDFEKKYPELYQANPHALKLEALKSGFSGKSVKKGL
GVFHIGNLGHYRDHKPVILHVIMGLTVGLAECRGTLAERCKVIKALGNPITQYCNKPYDTCQ
DYFDARNYLLPMKDQLKNPHAHHDACRTILLNCLFFKHRNYITSDCVPLVALCYLRVRQNF
VEAIMTEALRGEINTKGAAAAMKKVCEKIGHESPDLLHLCFKTTVLEKPKRSNKQYIEDVKS
RIRTVSTGNCRQVLEECYFNVLDYPDIYQSCRNFRRFCSEIGVVYTPVDSTFDLFQKPLSAEKL
LIDTSSKISEDLGLGFSKYVQKKSSNLEIAAYLVN[Forward2]KTWVYDND[Forward3]CRNKLKELCLH
IASLPLTKQLCTLAHDRNSKLCRDFYNSIGTECYSLYYEFKNVGLLYNYTYRLSRDQCSKYV
ERCLFLREQYAYWNSLDTC[Forward4]ANVFSSCYKEDMD[Reverse3]FSAKLDLLNRIKDKIVVPKGN
TRYFVELLCKSYTVAECSASDLMFKSYALMEACLHPERICRELKNHFSEESRKLENKLRSILKP
TYYECKDLGQK[Reverse2]CNSGFYFDGDIEAQCNHFKKRCQDKQERLKLINHIVDSSALYLANE
VQCRTYFDSFCGANVKQEFKQICNKGANGICPDIIDDSKEHCAHLINHLTSLGISSSSASLPLD
YCDSAINYCNSLSKFCTESKRQCDSVISFCTSESKKTDEYGSFIDQYPAAAANATKCKVTLKE
LCQDSSKKDSYSTLCAYNKDGYTEICKNLRNFIEKACENLRIHLHTYDTNSLNTNKGSAQDR
CTYIRNLYFKFKNICLLVDPFYDLSPIITQECKTNISEPALPDKDPQPTSSPQPKPRPRPRPQPQP
HPHPKPQPQPTPEPQPQPAPEPRPQPTSKPRPQPTSKPRPQPTPEPRPLPVPGPGPLPVPGPRPQP
QPQPQPQPQPQPQPQPQPQPQPQPQPQPQPKPQPPSQSTSESASQSKPKPTTQTKPSPRPHP
KPVPKPSSIDTGPSKSDSSFIFTVTKTITKISETEKPSTKPSVKPTSTKTTSKPSTKPSTKPSVKPA
STKTTSESEKPTLEEVPETKGNGVRVIGFEGLQLLSMIVAIIIGIWI[Reverse1]M

Figure 9

| Primer Pairs Utilized for PCR and Cloning |
|---|
| •Forward 1 + Reverse 3 → 1086 AA (3258 bp) |
| •Forward 2 + Reverse 2 → 117 AA (351 bp) |
| •Forward 2 + Reverse 1 → 213 AA (639 bp) |
| •Forward 3 + Reverse 2 → 112 AA (336 bp) |
| •Forward 3 + Reverse 1 → 208 AA (624 bp) |
| •Forward 4 + Reverse 1 → 115 AA (345 bp) |

Figure 10

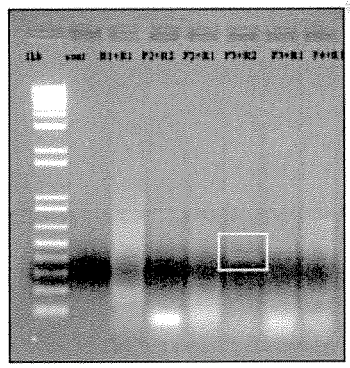

Figure 11

A12 Protein Region
KTWVYDND CRNKLKELCLHIASLPLTKQLCTLAHDRNSKLCRDFYNSIGTECYSLYYEF
KNVGLLYNYTYRLSRDQCSKYVERCLFLREQYAYWNSLDTCANVFSS CYKEDMD

Clone 2 Infected Human (3'-5' direction)
LLCSMEVVFKKDHSEHKYVEKKETEAANPLKAQAWKSQDVPATISYWSKQSQGQPRE
GVDMFHLLM

Clone 3 Infected Human (3'-5' direction)
CSMEVVFKKDHSEHKYVEKKETEAANPLKAQAWKSQDVPATISYWSKQSQGQPREGV
DMFXLLM

BLAST Alignment of Homology
```
Query   15    KYVEKKETEAANPLKAQ--AWKSQDVPATI    42
              KYVE+        L+ Q    W S D  A +
Sbjct   79    KYVER-----CLFLREQYAYWNSLDTCANV   103
```

Figure 12

|  | 2000 Wakefield Primer | 2012 F3/R2 Degenerate Primer |
|---|---|---|
| 2012 AA Wakefield | (10/ 19) | (9/ 19) |
|  | 52.60% | 47.40% |

OPTIMIZED ANTIGENS OF PNEUMOCYSTIS AND USE THEREOF

This application is a national stage application under 35 U.S.C. 371 from PCT Application No. PCT/US2012/049758, filed Aug. 6, 2012, which claims the priority benefit of U.S. Provisional Patent Application Ser. No. 61/515,133, filed Aug. 4, 2011 which is hereby incorporated by reference in its entirety.

This invention was made with government support under grant number AI023302 awarded by the National Institutes of Health. The government has certain rights in the invention.

FIELD OF THE INVENTION

The present invention relates to optimized antigens of *Pneumocystis* and methods of their use.

BACKGROUND OF THE INVENTION

*Pneumocystis* entered the spotlight of public health as the hallmark of HIV infection. As research on the fungus expanded, *Pneumocystis* pneumonia was found to infect a variety of patients with the commonality of a suppressed immune system. As the length of survival in AIDS, cancer, transplant, and other immunosuppressed patients has been prolonged, the prevalence rate of *Pneumocystis* pneumonia in the population also has increased. Treatments for *Pneumocystis* pneumonia in such individuals often cause adverse side effects and are not always effective. Therefore, developing an effective vaccine is of great interest for researchers and the medical community.

*Pneumocystis* cannot be continuously cultured outside of its host. *Pneumocystis* also has a host species-dependent specificity which complicates the ability to use animal derived organisms to immunize humans. *Pneumocystis* organisms derived from different hosts have isoform variants of common antigens resulting in different (i.e., non-crossreactive) antigenic determinants (Gigliotti et al., "Antigenic Characterization of *Pneumocystis carinii*," *Semin. Respir. Infect.* 13:313-322 (1998); Gigliotti et al., "Further Evidence of Host Species-Specific Variation in Antigens of *Pneumocystis carinii* Using the Polymerase Chain Reaction," *J. Infect. Dis.* 168:191-194 (1993)). Attempts to infect laboratory animals with *Pneumocystis* isolated from heterologous mammalian species have met with little to no success (Aliouat et al., "*Pneumocystis* Cross Infection Experiments Using SCID Mice and Nude Rats as Recipient Host, Showed Strong Host-Species Specificity," *J. Eukaryot. Microbiol.* 41:71S (1994); Atzori et al., "*P. carinii* Host Specificity: Attempt of Cross Infections With Human Derived Strains in Rats," *J. Eukaryot. Microbiol.* 46:112S (1999); Gigliotti et al., "*Pneumocystis carinii* Host Origin Defines the Antibody Specificity and Protective Response Induced by Immunization," *J. Infect. Dis.* 176:1322-1326 (1997)). However, immunocompetent mice immunized with whole mouse *Pneumocystis* are protected from developing *Pneumocystis* pneumonia after T cell depletion and subsequent challenge, whereas unimmunized cohorts are not protected (Harmsen et al., "Active Immunity to *Pneumocystis carinii* Reinfection in T-cell-depleted Mice," *Infect. Immun.* 63:2391-2395 (1995)).

The surface glycoprotein gpA is an abundant and immunodominant antigen of *Pneumocystis* (Graves et al., "Development and Characterization of Monoclonal Antibodies to *Pneumocystis carinii*," *Infect. Immun.* 51:125-133 (1986)), although immunization with this antigen does not adequately protect against infection in a mouse model of *Pneumocystis* pneumonia (Gigliotti et al., "Immunization with *Pneumocystis carinii* gpA is Immunogenic But Not Protective in a Mouse Model of *P. carinii* Pneumonia," *Infect. Immun.* 66:3179-3182 (1998)). The majority of monoclonal antibodies ("mAb") against *Pneumocystis* surface antigens react with only isoforms showing host species-specificity identical to that of the immunogen (Gigliotti et al., "*Pneumocystis carinii* Host Origin Defines the Antibody Specificity and Protective Response Induced by Immunization," *J. Infect. Dis.* 176:1322-1326 (1997)). mAb4F11 was obtained by selective screening of anti-mouse *Pneumocystis* hybridomas for recognition of *Pneumocystis* antigens other than gpA (Lee et al., "Molecular Characterization of KEX1, a Kexin-Like Protease in Mouse *Pneumocystis carinii*," *Gene* 242:141-150 (2000)). mAb4F11 confers passive prophylaxis against development of *Pneumocystis* pneumonia when administered intranasally to SCID mice (Gigliotti et al., "Passive Intranasal Monoclonal Antibody Prophylaxis Against Murine *Pneumocystis carinii* Pneumonia," *Infect. Immun.* 70:1069-1074 (2002)). Furthermore, mAb4F11 recognizes surface antigens of *Pneumocystis* derived from different hosts, including humans. A screen of a *Pneumocystis* cDNA expression library using mAb4F11 revealed a number of positive clones, including mouse *Pneumocystis* Kex1 (Lee et al., "Molecular Characterization of KEX1, a Kexin-Like Protease in Mouse *Pneumocystis carinii*," *Gene* 242:141-150 (2000)). Based on sequence homology to its ortholog in *Saccharomyces cerevisiae*, Kex1 is a member of the kexin family of subtilisin-like proteases (Lee et al., "Molecular Characterization of KEX1, a Kexin-Like Protease in Mouse *Pneumocystis carinii*," *Gene* 242:141-150 (2000)).

CD4 depletion models in mice are designed to mimic individuals with a suppressed adaptive immune response. Injecting with whole *Pneumocystis* has been shown to provide sterilizing immunity in such immunocompromised mice. However, due to a variety of factors, whole *Pneumocystis* is not a viable vaccine option in humans. Extensive studies of antibodies to *Pneumocystis* led to the discovery of the monoclonal antibody 4F11, which is of great scientific relevance because it provides protection against the development of *Pneumocystis* pneumonia via passive prophylaxis and cross reacts with human-derived *Pneumocystis*. 4F11 recognizes an epitope that is present on two distinct antigens in mouse-derived *Pneumocystis*: Kexin and A12. Further analysis showed the 4F11 epitope is on the C-terminal half of the A12 gene. This makes the A12 antigen a candidate for a potential vaccine.

However, attempts to produce a full-length A12 protein in large quantities in yeast and *E. coli* have been unsuccessful thus far due to problematic codons at the N-terminus.

The present invention is directed to overcoming these and other deficiencies in the art.

SUMMARY OF THE INVENTION

One aspect of the present invention relates to an isolated *Pneumocystis* A12 protein comprising more than 230 amino acid residues, where the isolated A12 protein has an amino acid sequence that is at least 20% identical to SEQ ID NO: 1.

Another aspect of the present invention relates to an isolated nucleic acid molecule that encodes an amino acid sequence that is at least 20% identical to the amino acid sequence of SEQ ID NO: 1.

A further aspect of the present invention relates to a fusion protein comprising a first protein or protein fragment comprising an N-terminal region of *Pneumocystis* A12 and a second protein or protein fragment linked to the first protein or protein fragment.

Another aspect of the present invention relates to an isolated nucleic acid molecule that encodes the fusion protein of the present invention.

A further aspect of the present invention relates to an isolated *Pneumocystis* A12 protein or polypeptide comprising an amino acid sequence that is at least 20% identical to residues 1-457 of SEQ ID NO:1.

Another aspect of the present invention relates to an isolated nucleic acid molecule that encodes a *Pneumocystis* A12 protein or polypeptide comprising an amino acid sequence that is at least 20% identical to residues 1-457 of SEQ ID NO:1.

A further aspect of the present invention relates to an isolated *Pneumocystis* A12 protein or polypeptide fragment having an amino acid sequence that is at least 30% identical to a 25 contiguous amino acid sequence of SEQ ID NO:2.

Another aspect of the present invention relates to an isolated nucleic acid molecule that encodes a *Pneumocystis* A12 protein or polypeptide fragment having an amino acid sequence that is at least 30% identical to a 25 contiguous amino acid sequence of SEQ ID NO:2.

A further aspect of the present invention relates to expression systems comprising any one of the nucleic acid molecules of the present invention in a heterologous vector, and host cells comprising any of the nucleic acid molecules or expression systems of the present invention.

Another aspect of the present invention relates to a vaccine comprising any of the isolated *Pneumocystis* A12 protein or polypeptide of the present invention.

A further aspect of the present invention relates to a method of immunizing a subject against infection of *Pneumocystis*. This method involves administering the vaccine of the present invention to a subject under conditions effective to immunize the subject against infection of *Pneumocystis*.

Another aspect of the present invention relates to a pharmaceutical composition comprising any of the isolated *Pneumocystis* A12 protein or polypeptide of the present invention and a pharmaceutically acceptable carrier.

A further aspect of the present invention relates to an immunogenic conjugate comprising any of the isolated *Pneumocystis* A12 protein or polypeptide of the present invention covalently or non-covalently bonded to a carrier molecule.

Another aspect of the present invention relates to a pharmaceutical composition comprising an immunogenic conjugate of the present invention and a pharmaceutically acceptable carrier.

A further aspect of the present invention relates to an antibody raised against any of the isolated *Pneumocystis* A12 protein or polypeptide of the present invention or an immunogenic conjugate comprising any of said isolated *Pneumocystis* A12 protein or polypeptide covalently or non-covalently bonded to a carrier molecule, where the antibody binds specifically to an epitope comprising amino acid residues within a region of 1-821 of SEQ ID NO:1.

Another aspect of the present invention relates to an antiserum comprising an antibody of the present invention.

A further aspect of the present invention relates to a pharmaceutical composition comprising an antibody of the present invention and a pharmaceutically acceptable carrier.

Another aspect of the present invention relates to a method of treating or preventing infection in a subject by a *Pneumocystis* organism. This method involves administering to a subject an amount of (i) a first antibody raised against any of the isolated *Pneumocystis* A12 protein or polypeptide of the present invention where the antibody binds specifically to an epitope comprising amino acid residues within a region of 1-821 of SEQ ID NO: 1; (ii) a second antibody raised against an immunogenic conjugate comprising any of said isolated *Pneumocystis* A12 protein or polypeptide of the present invention covalently or non-covalently bonded to a carrier molecule; or (iii) any combination thereof, where the amount is effective to treat or prevent infection by a *Pneumocystis* organism.

A further aspect of the present invention relates to a diagnostic kit comprising either an antibody raised against any of the isolated *Pneumocystis* A12 protein or polypeptide of the present invention, where the antibody binds specifically to an epitope comprising amino acid residues within a region of 1-821 of SEQ ID NO:1, an antibody raised against an immunogenic conjugate comprising any of said isolated *Pneumocystis* A12 protein or polypeptide of the present invention, or both.

Expression of the full-length A12 protein has resulted in detectable protein, but the yields are too low to produce for vaccine trials; instead, the protein was expressed as two half-length segments. The C terminal half of the protein (1650-3300 bp) expressed very well; however, the N terminal half (1-1650) was not well expressed. For immunization studies, the N-terminal half was expressed as a thioredoxin fusion protein and found to give significant protection, but it does not contain the 4F11 mAb epitope. In order to preserve the 4F11 epitope and remove the need for a thioredoxin fusion, a larger fragment of the A12 gene (bp 46-3300) was generated, omitting a cluster of problematic codons at the N-terminal end, in an attempt to produce enough protein for immunization.

As described herein, A12 has been produced as two half-length clones and protein expression was induced to generate antigen for immunization. Immunizing with a Thioredoxin fusion with the N-terminal half protein resulted in significant protection. To further evaluate the vaccination capability of the A12 antigen, the experiments described in the Examples were conducted to produce a larger segment of the protein, omitting fifteen problematic codons at the N-terminus. The resulting A12 fragment can be used in immunization studies.

BRIEF DESCRIPTION OF THE DRAWINGS

FIG. 3 shows the full-length amino acid sequence of the A12 protein from mouse-derived *Pneumocystis* (SEQ ID NO: 1). Amino acids shown in light shading (i.e., SEQ ID NO:2) represent the primary structure of the Thioredoxin fusion N-terminal half-protein. Amino acids shown in dark shading (i.e., SEQ ID NO:3) represent the primary structure of the C-terminal half of the protein. Amino acids shown in bold italic type are carried by rare tRNAs, causing problematic translation of the N-terminal region of the protein. The arrow indicates the first amino acid included in the $A12_{46-3297}$ protein (i.e., SEQ ID NO:4). The 4F1 epitope is underlined.

FIG. 4 is a timeline of treatments of CB 17 WT mice for immunization studies. Boosts at day 21 and 42 were matched to treatment given at day 0. Sera was collected after the 1st boost and the 2nd boost to check for antibody production.

FIGS. 7A-D are images of Immunofluorescence Assay ("IFA") results for mouse-derived *Pneumocystis* with sera. FIGS. 7A-C show IFA results with sera from mice immunized with Thioredoxin, Thioredoxin:N-terminal half, or both C-terminal half and Thioredoxin:N-terminal half, respectively. FIG. 7D shows IFA results with sera from mice immunized with whole *Pneumocystis*.

FIG. 9 shows A12 protein from mouse (SEQ ID NO: 1). Highlighted regions illustrate homology between mouse and rat. Forward Degenerate Primers and Reverse Degenerate Primers are shown.

FIG. 10 shows suggested primer pairs to utilize for PCR and cloning. Each primer pair corresponds to a region on the A12 protein of FIG. 9.

FIG. 11 shows PCR results from each primer pair with infected human Pj DNA (1:40 dilution) on a 1.2% TAE gel to determine which primer pair gives rise to the appropriate band size. Primer pair F3+R2 gave a product of the predicted size.

FIG. 12 shows the A12 region of interest (SEQ ID NO:11) (between degenerate primer pair F3 and R2) with the sequenced clones 2 (SEQ ID NO: 12) and 3 (SEQ ID NO: 13) from infected human *Pneumocystis* that had a 43% query match. Primers highlighted; exact amino acid match highlighted; + indicates similar amino acid match.

DETAILED DESCRIPTION OF THE INVENTION

Figures 1, 2:
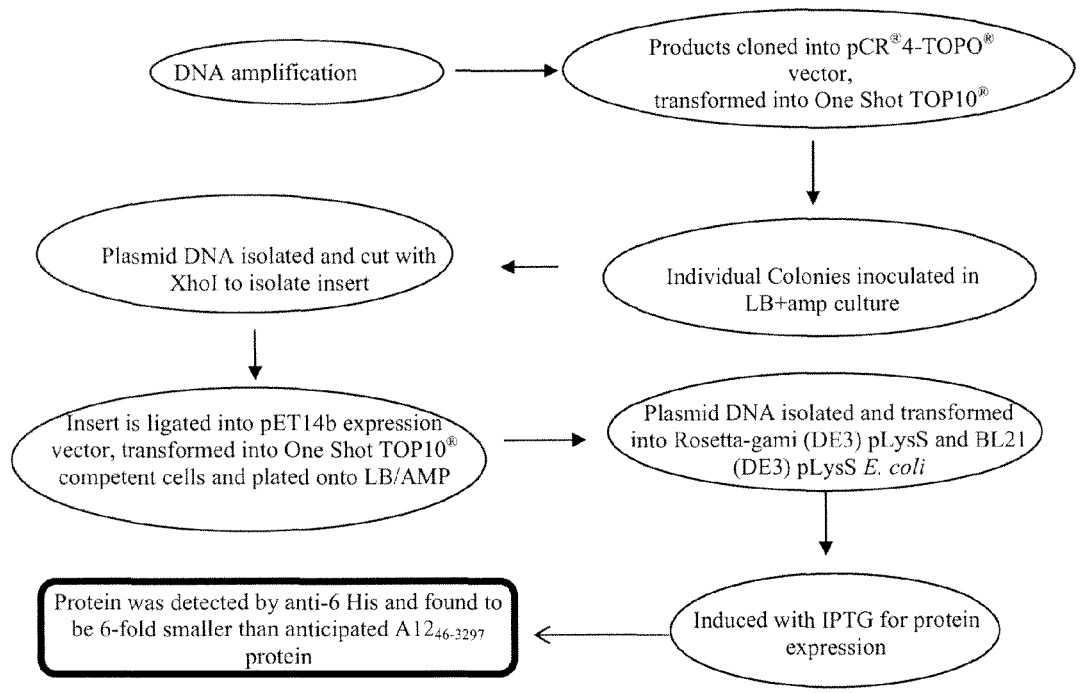
FIG. 1 is a flow chart of cloning procedures of $A12_{46-3297}$ clones.
FIG. 2 is a table showing the experimentally determined codon bias of *E. coli* and the distribution of the problematic codons on the N- and C-terminal halves of A12.

The present invention relates to a number of isolated *Pneumocystis* A12 proteins and polypeptides and isolated nucleic acid molecules that encode the *Pneumocystis* A12 proteins or polypeptides of the present invention.

As used herein, *Pneumocystis* refers to *Pneumocystis* organisms derived from a variety of species, including mammals, such as mouse-, rat-, and human-derived *Pneumocystis*.

While an isolated C-terminal fragment of *Pneumocystis* A12 protein has previously been identified (see GenBank Accession No. AY371664 and U.S. Pat. No. 7,815,918, which are hereby incorporated by reference in their entirety), the present invention describes the first isolated full-length *Pneumocystis* A12 protein, including an N-terminal fragment, fusion proteins with either an N- or C-terminal half of A12, and partial sequences.

A first aspect of the present invention relates to an isolated *Pneumocystis* A12 protein comprising more than 230 amino acid residues, where the isolated A12 protein has an amino acid sequence that is at least 20% identical to SEQ ID NO:1.

SEQ ID NO:1 (i.e., the full sequence shown in FIG. 3) is a full-length mouse-derived *Pneumocystis* A12 protein. The present invention is directed to homologs of the mouse *Pneumocystis* A12 protein (i.e., *Pneumocystis* A12 proteins derived from other organisms, including other mammals, particularly human derived *Pneumocystis* A12 protein). Hence, in one embodiment, the present invention is directed to an isolated *Pneumocystis* A12 protein having an amino acid sequence that is at least 20% identical to SEQ ID NO:1.

One example of a human-derived *Pneumocystis* A12 protein fragment is illustrated in SEQ ID NO:6, as follows:

```
LLCSMEVVFK KDHSEHKYVE KKETEAANPL KAQAWKSQDV

PATISYWSKQ SQGQPREGVD MFHLLM
```

In other embodiments, this aspect of the present invention is directed to an isolated *Pneumocystis* A12 protein comprising more than 230 amino acid residues, e.g., comprising more than 231, 232, 233, 234, 235, 236, 237, 238, 239, 240, 241, 242, 243, 244, 245, 250, 260, 270, 280, 290, 300, 325, 350, 375, 400, 500, 600, 700, or 800 amino acid residues, where the isolated protein (of any of the above-recited lengths) has an amino acid sequence that is at least 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to SEQ ID NO:1.

Percent identity as used herein refers to the comparison of one amino acid (or nucleic acid) sequence to another, as scored by matching amino acids (or nucleic acids). Percent identity is determined by comparing a statistically significant number of the amino acids (or nucleic acids) from two sequences and scoring a match when the same two amino acids (or nucleic acids) are present at a position. The percent identity can be calculated by any of a variety of alignment algorithms known and used by persons of ordinary skill in the art.

Another aspect of the present invention relates to an isolated nucleic acid molecule that encodes the above isolated protein. In one embodiment of this aspect of the present invention, the nucleic acid molecule is the nucleic acid molecule encoding the full-length mouse-derived *Pneumocystis* A12 protein of SEQ ID NO:5, as follows:

```
ATGTTTTTCT TAAGAATCAT CTTTATATTT ATTTTTTAA

AAATATCATA TGCAGAAAAC ACAGATAAAC TCTCAGATTT

CGAAAAAAAA TATCCAGAAT TATATCAAGC AAATCCACAT

GCTTTAAAAC TGGAAGCATT GAAAAGCGGA TTTTCAGGCA

AATCTGTAAA AAAAGGATTG GGTGTTTTTC ATATAGGGAA

TCTTGGTCAT TATAGAGATC ATAAACCAGT TATATTGCAT
```

-continued
```
GTAATTATGG GATTAACTGT TGGACTCGCA GAGTGTCGCG
GGACACTCGC CGAAAGATGT AAAGTCATAA AAGCCCTAGG
AAATCCAATA ACACAATATT GCAATAAACC ATATGATACA
TGCCAAGATT ATTTTGACGC TCGAAATTAC TTACTCCCTA
TGAAAGATCA ATTAAAAAAC CCACACGCCC ATCATGATGC
ATGCAGAACG ATTTTGCTAA ATTGCCTCTT TTTTAAACAT
CGTAATTATA TTACTTCCGA TTGTGTTCCT TTGGTAGCAT
TATGTTATTT GCGGGTTCGT CAAAAGTTTG TAGAAGCAAT
TATGACCGAA GCATTAAGAG GGGAAATTAA TACTAAGGGT
GCTGCTGCAG CAATGAAAAA AGTATGTGAA AAAATTGGAC
ATGAGAGTCC GGACTTGCTT CATTTATGTT TTAAGACCAC
TGTATTAGAA AAACCTAAAA GGTCTAATAA ACAGTATATT
GAAGATGTTA AGTCAAGAAT AAGGACAGTT TCGACTGGAA
ATTGCCGTCA GGTTTTGGAA GAATGCTATT TTAATGTTCT
AGATTATCCA GATATTTATC AATCATGTAG GAATTTTCGA
CGATTCTGTT CAGAAATAGG AGTTGTATAT ACTCCAGTCG
ATTCCACTTT TGATTTATTT CAGAAGCCCC TTTCTGCAGA
AAAGTTACTA ATTGATACTT CTTCAAAAAT CTCAGAAGAC
TTAGGTCTTG GTTTTTCTAA ATATGTACAA AAAAAATCAA
GCAATCTTGA GATTGCGGCA TATTTAGTTA ATAAGACTTG
GGTCTATGAT AATGATTGCA GAAATAAATT AAAAGAACTA
TGTCTGCATA TTGCTTCTCT ACCGCTTACA AAACAACTAT
GCACATTAGC ACATGATAGA AATTCGAAAC TCTGTAGGGA
TTTTTATAAC TCTATTGGGA CTGAATGCTA TTCTTTATAT
TATGAATTTA AGAATGTTGG ATTATTATAC AATTATACTT
ATCGTCTTTC AAGAGATCAA TGCTCTAAAT ATGTAGAAAG
ATGTCTTTTT CTTAGGGAGC AAATATGCTTA TTGGAATTCT
CTAGATACTT GTGCTAATGT ATTTTCTTCA TGTTATAAAG
AAGATATGGA TTTTTCAGCC AAATTAGATC TTCTAAATAG
GATAAAAGAT AAGATTGTAG TTCCAAAAGG AAACACGAGG
TATTTGTAG AGTTATTGTG TAAAAGCTAT ATTGTCGCCG
AATGCAGCGC CAGTGATTTA ATGTTCAAAT CTTATGCTCT
TATGGAAGCC TGTCTTCACC CAGAAAGGAT CTGTAGAGAA
TTAAAAAATC ATTTTTCCGA AGAATCTAGG AAATTAGAAA
ATAAATTAAG GAGTATTTTA AAACCCACAT ATTATGAATG
CAAAGATCTA GGACAAAAGT GCAACTCTGG ATTTTATTTT
GATGGAGATA TAGAAGCTCA ATGCAATCAT TTCAAAAAAA
GATGTCAAGA TAAACAAGAG AGACTAAAAT TAATTAATCA
TATTGTTGAT TCATCTGCTC TTTATCTCGC AAATGAAGTA
CAATGCAGAA CTTATTTCGA CAGTTTTTGT GGTGCGAATG
TAAAACAAGA ATTCAAACAA ATATGCAACA AAGGAGCTAA
TGGCATATGC CCTGATATAA TAGATGATTC TAAAGAACAT
TGTGCTCATT TGATTAATCA TTTAACATCT CTTGGAATTT
CATCGTCTTC TGCTTCACTT CCATTGGACT ATTGCGACTC
AGCGATTAAT TACTGTAATT CTCTTTCGAA GTTTTGCACG
GAATCAAAAC GACAGTGCGA TTCTGTTATT TCTTTCTGCA
CTAGCGAATC AAAAAAAACT GATGAATATG GTTCTTTTAT
TGACCAATAT CCCGCGGCTG CAGCAAATGC AACCAAATGC
AAGGTAACTT TGAAAGAGTT ATGCCAAGAT TCAAGCAAAA
AAGACTCTTA TTCAACACTA TGTGCTTATA ATAAAGATGG
TTATACCGAA ATATGTAAAA ACTTAAGAAA TTTCATAGAA
AAAGCATGCG AGAATTTGAG AATTCATTTA CATACTTATG
ATACAAACTC ACTCAATACG AATAAAGGAT CTGCTCAAGA
TAGATGCACT TATATAAGAA ATCTTTACTT TAAATTTAAA
AATATATGTT TATTGGTTGA TCCTTTCTAT GACTTATCTC
CTATTATCAC TCAAGAATGT AAAACCAATA TATCCGAACC
AGCACTGCCT GATAAGGATC CTCAACCTAC ATCTTCACCT
CAGCCAAAAC CTCGGCCAAG ACCTCGACCT CAACCTCAAC
CTCATCCACA TCCAAAACCT CAGCCTCAGC CGACGCCAGA
ACCTCAGCCT CAGCCGGCGC CAGAACCTCG ACCTCAGCCG
ACGTCAAAAC CTCGACCTCA GCCAACGTCA AAACCTCGAC
CTCAGCCGAC GCCAGAACCT CGACCTCTGC CGGTGCCAGG
ACCTGGACCT CTGCCGGTGC CAGGACCTCG ACCTCAACCT
CAACCTCAAC CTCAACCTCA GCCTCAACCT CAACCTCAGC
CTCAACCTCA ACCTCAGCCT CAGCCTCAGC CTCAGCCTCA
GCCTCAACCT CAGCCGAAGC CTCAACCACC ATCTCAGTCA
ACATCAGAAT CAGCATCGCA ATCCAAACCA AAACCAACAA
CACAAACAAA ACCGTCACCG AGACCACACC CAAAGCCGGT
GCCAAAACCA TCATCGATAG ACACAGGACC ATCAAAATCG
GATTCAAGCT TCATTTTTAC AGTAACAAAA ACAATAACAA
AGATATCAGA AACAGAAAAA CCATCTACAA AACCATCTGT
GAAACCAACC TCTACAAAGA CAACATCAAA ACCATCTACA
AAACCATCTA CAAAACCATC TGTAAAACCA GCCTCTACAA
AGACAACATC AGAATCAGAA AAACCAACAT GGAAGAAGT
TCCAGAAACT AAAGGGAATG GTGTAAGAGT AATAGGATTT
GAGGGGTTAC AATTATTATC AATGATTGTT GCAATAATAA
TTGGGATATG GATAATGTAA
```

A further aspect of the present invention relates to a fusion protein comprising a first protein or protein fragment comprising an N-terminal region of *Pneumocystis* A12 and a second protein or protein fragment linked to the first protein or protein fragment.

According to this aspect of the present invention, the N-terminal region of *Pneumocystis* A12 comprises an amino acid sequence that is at least about 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to an N-terminal portion of SEQ ID NO:1.

An N-terminal region of *Pneumocystis* A12 includes, for example, a contiguous number of residues within amino acids 1-475 or 1-821 of SEQ ID NO: 1. For example, the N-terminal region of *Pneumocystis* A12 comprises an amino acid sequence that is at least about 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to a contiguous amino acid sequence of at least about 25, 26, 27, 28, 29, 30, 31, 32, 33, 34, 35, or at least about 40, 45, 50, 55, 60, 65, 70, 75, 80, 85, 90, 95, or at least about 100 contiguous residues of amino acids 1-475 or 1-821 of SEQ ID NO:1, which form a protective epitope. A protective epitope induces a protective immune response against *Pneumocystis*.

In yet another alternative embodiment, the fusion protein of the present invention comprises a protein or polypeptide that is at least 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to SEQ ID NO:2. SEQ ID NO:2 is the N-terminal portion of SEQ ID NO: 1, which is illustrated in FIG. 3 in light shading, and which has the following sequence:

```
MFFLRIIFIF IFLKISYAEN TDKLSDFEKK YPELYQANPH

ALKLEALKSG FSGKSVKKGL GVFHIGNLGH YRDHKPVILH

VIMGLTVGLA ECRGTLAERC KVIKALGNPI TQYCNKPYDT

CQDYFDARNY LLPMKDQLKN PHAHHDACRT ILLNCLFFKH

RNYITSDCVP LVALCYLRVR QNFVEAIMTE ALRGEINTKG

AAAAMKKVCE KIGHESPDLL HLCFKTTVLE KPKRSNKQYI

EDVKSRIRTV STGNCRQVLE ECYFNVLDYP DIYQSCRNFR

RFCSEIGVVY TPVDSTFDLF QKPLSAEKLL IDTSSKISED

LGLGESKYVQ KKSSNLEIAA YLVNKTWVYD NDCRNKLKEL

CLHIASLPLT KQLCTLAHDR NSKLCRDFYN SIGTECYSLY

YEFKNVGLLY NYTYRLSRDQ CSKYVERCLF LREQYAYWNS

LDTCANVFSS CYKEDMDFSA KLDLLNRIKD KIVVP
```

The second protein or protein fragment in the fusion protein of the present invention may be any protein or protein fragment that, in combination with the N-terminus region of *Pneumocystis* A12 gives a protective immune response to infection by *Pneumocystis* in a subject. In one embodiment, the second protein or protein fragment is a thioredoxin protein. Other suitable second protein or protein fragments may be bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

Another aspect of the present invention relates to an isolated nucleic acid molecule that encodes the fusion protein of the present invention.

A further aspect of the present invention relates to an isolated *Pneumocystis* A12 protein or polypeptide comprising an amino acid sequence that is at least 20% identical to residues 17-457 of SEQ ID NO:1.

In one embodiment, this isolated *Pneumocystis* A12 protein or polypeptide has an amino acid sequence that is at least about 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to residues 17-457 of SEQ ID NO:1.

In another embodiment, this isolated *Pneumocystis* A12 protein or polypeptide has an amino acid sequence that is at least about 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to residues 17-475 of SEQ ID NO: 1.

In a further embodiment, this isolated *Pneumocystis* A12 protein or polypeptide has an amino acid sequence that is at least about 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to residues 17-821 of SEQ ID NO: 1.

In yet another embodiment, this isolated *Pneumocystis* A12 protein or polypeptide has an amino acid sequence that is at least about 20%, 21%, 22%, 23%, 24%, 25%, 26%, 27%, 28%, 29%, 30%, 31%, 32%, 33%, 34%, 35%, 36%, 37%, 38%, 39%, 40%, 50%, 60%, 70%, 80%, or 90% identical to SEQ ID NO:4. SEQ ID NO:4 has a sequence as follows:

```
YAENTDKLSD FEKKYPELYQ ANPHALKLEA LKSGFSGKSV

KKGLGVFHIG NLGHYRDHKP VILHVIMGLT VGLAECRGTL

AERCKVIKAL GNPITQYCNK PYDTCQDYFD ARNYLLPMKD

QLKNPHAHHD ACRTILLNCL FFKHRNYITS DCVPLVALCY

LRVRQNFVEA IMTEALRGEI NTKGAAAAMK KVCEKIGHES

PDLLHLCEKT TVLEKPKRSN KQYIEDVKSR IRTVSTGNCR

QVLEECYFNV LDYPDIYQSC RNFRRFCSEI GVVYTPVDST

FDLFQKPLSA EKLLIDTSSK ISEDLGLGFS KYVQKKSSNL

EIAAYLVNKT WVYDNDCRNK LKELCLHIAS LPLTKQLCTL

AHDRNSKLCR DFYNSIGTEC YSLYYEFKNV GLLYNYTYRL

SRDQCSKYVE RCLFLREQYA YWNSLDTCAN VFSSCYKEDM

DFSAKLDLLN RIKDKIVVPK GNTRYFVELL CKSYIVAECS

ASDLMFKSYA LMEACLHPER ICRELKNHFS EESRKLENKL

RSILKPTYYE CKDLGQKCNS GFYFDGDIEA QCNHEKKRCQ

DKQERLKLIN HIVDSSALYL ANEVQCRTYF DSFCGANVKQ

EFKQICNKGA NGICPDIIDD SKEHCAHLIN HLTSLGISSS

SASLPLDYCD SAINYCNSLS KFCTESKRQC DSVISFCTSE

SKKTDEYGSF IDQYPAAAAN ATKCKVTLKE LCQDSSKKDS

YSTLCAYNKD GYTEICKNLR NFIEKACENL RIHLHTYDTN

SLNTNKGSAQ DRCTYIRNLY FKFKNICLLV DPFYDLSPII

TQECKTNISE PALPDKDPQP TSSPQPKPRP RPRPQPQPHP

HPKPQPQPTP EPQPQPAPEP RPQPTSKPRP QPTSKPRPQP

TPEPRPLPVP GPGPLPVPGP RPQPQPQPQP QPQPQPQPQP

QPQPQPQPQP QPQPQPKPQP PSQSTSESAS QSKPKPTTQT
```

-continued

```
KPSPRPHPKP VPKPSSIDTG PSKSDSSFIF TVTKTITKIS

ETEKPSTKPS VKPTSTKTTS KPSTKPSTKP SVKPANHSTK

TTSESEKPTL EEVPETKGNG VRVIGFEGLQ LLSMIVAIII

GIWIM
```

SEQ ID NO:4 is also described herein as $A12_{46-3297}$.

Another aspect of the present invention relates to an isolated nucleic acid molecule that encodes the above *Pneumocystis* A12 protein or polypeptide.

A further aspect of the present invention relates to an isolated *Pneumocystis* A12 protein or polypeptide fragment comprising an amino acid sequence that is at least 20% identical to a 25 contiguous amino acid sequence of SEQ ID NO:2. In one embodiment, the isolated *Pneumocystis* A12 protein or polypeptide fragment comprises an amino acid sequence that is at least about 20%, 21%, 22%, 23%, 24%, 25%, 26%, 27%, 28%, 29%, 30/o, 31%, 32%, 33%, 34%, 35%, 36%, 37%, 38%, 39%, 40%, 50%, 60%, 70%, 80%, or 90% identical to a contiguous amino acid sequence of at least about 25, 26, 27, 28, 29, 30, 31, 32, 33, 34, 35, or at least about 40, 45, 50, 55, 60, 65, 70, 75, 80, 85, 90, 95, or at least about 100 contiguous residues of SEQ ID NO:2.

Another aspect of the present invention relates to an isolated nucleic acid molecule that encodes such fragment.

A further aspect of the present invention relates to expression systems comprising any one of the nucleic acid molecules of the present invention (i.e., nucleic acid molecules that encode the *Pneumocystis* A12 protein or polypeptide of the present invention) in a heterologous vector and host cells comprising any of the nucleic acid molecules of the present invention.

Expression of a *Pneumocystis* A12 protein or polypeptide of the present invention can be carried out by introducing a nucleic acid molecule encoding the *Pneumocystis* A12 protein or polypeptide into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'-+3') orientation and correct reading frame. The vector contains the necessary elements for the transcription and translation of the inserted *Pneumocystis* A12 protein or polypeptide coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pFastBac series (Invitrogen), pET series (see F. W. Studier et. al., "Use of T7 RNA Polymerase to Direct Expression of Cloned Genes," *Gene Expression Technology Vol.* 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the *Pneumocystis* A12 protein or polypeptide-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, recA promoter, ribosomal RNA promoter, the $P_R$ and $P_L$ promoters of coliphage lambda and others including, but not limited to, lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The *Pneumocystis* A12 protein or polypeptide-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a *Pneumocystis* A12 protein or polypeptide of the present invention is inserted into a vector in the sense (i.e., 5'→3') direction, such that the open reading frame is properly oriented for the expression of the encoded *Pneumocystis* A12 protein or polypeptide of the present invention under the control of a promoter of choice. Single or multiple nucleic acids may be ligated into an appropriate vector in this way, under the control of a suitable promoter, to prepare a nucleic acid construct.

Once the isolated nucleic acid molecule encoding the *Pneumocystis* A12 protein or polypeptide of the present invention has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

A further aspect of the present invention relates to an immunogenic conjugate comprising any of the isolated *Pneumocystis* A12 protein or polypeptide of the present invention covalently or non-covalently bonded to a carrier molecule.

According to one embodiment, the immunogenic conjugate includes a carrier molecule to which the *Pneumocystis* A12 protein or polypeptide of the present invention is covalently or non-covalently bonded. Exemplary carrier molecules include, without limitation, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein. Each of these carrier molecules is safe for administration and immunologically effective; they are non-toxic and the incidence of allergic reaction is well known for each of them.

The immunogenic conjugate can further include a bacterial molecule covalently or non-covalently bonded to either the carrier molecule or the isolated protein or polypeptide (i.e., forming a three-component conjugate). Suitable bacterial molecules include, without limitation, lipopolysaccharides, polysaccharides that are distinct of the carrier molecules described above, or proteins or polypeptides that are distinct of both the isolated *Pneumocystis* A12 protein or polypeptide of the present invention and the carrier molecules described above.

When all components of the immunogenic conjugate are polypeptides, the immunogenic conjugate can take the form of a fusion or chimeric protein that includes the *Pneumocystis* A12 protein or polypeptide of the present invention coupled by an in-frame gene fusion to a carrier protein or polypeptide (as the carrier molecule). In this arrangement, the carrier protein or polypeptide can be any of the above-identified proteins or polypeptides, as well as plasmid-, chromosomal (prokaryotic or eukaryotic)- or viral-encoded carrier polypeptides or proteins.

An exemplary immunogenic conjugate of the present invention includes a *Pneumocystis* A12 protein or polypeptide of the present invention and a bacterial molecule covalently or non-covalently bonded to the carrier protein or polypeptide. The bacterial molecule can be any of the type identified above, but in one embodiment is a pneumococcal capsular polysaccharide, one or more meningococcal outer membrane proteins, or a combination thereof.

Immunogenic conjugates that are not fusion proteins per se, i.e., contain a non-proteinaceous component, can be formed using standard conjugation conditions. For example, according to one approach, conjugation can be achieved via an EDC-catalyzed amide linkage to the N-terminus of the *Pneumocystis* A12 protein or polypeptide of the present invention. Alternatively, conjugation can be achieved via aminoalkylation according to the Mannich reaction. Once these conjugates have been prepared, they can be isolated and purified according to standard procedures.

Immunogenic conjugates that are fusion proteins can be formed using standard recombinant DNA techniques as described supra. Basically, DNA molecules encoding the various polypeptide components of the immunogenic conjugate (to be prepared) are ligated together along with appropriate regulatory elements that provide for expression (i.e., transcription and translation) of the fusion protein encoded by the DNA molecule. When recombinantly produced, the immunogenic fusion proteins are expressed in a recombinant host cell, typically, although not exclusively, a prokaryote.

Another type of active agent is an antibody that can recognize (or bind to) *Pneumocystis* A12 protein or polypeptide, as described herein, either in whole or in part. Such antibodies of the present invention can be raised against the isolated *Pneumocystis* A12 protein or polypeptide of the present invention, or any immunogenic conjugates of the present invention.

The antibodies of the present invention can be either monoclonal antibodies, polyclonal antibodies, or functional fragments or variants thereof.

Monoclonal antibody production can be effected by techniques that are well-known in the art. Basically, the process involves first obtaining immune cells (lymphocytes) from the spleen of a mammal (e.g., mouse) that has been previously immunized with the antigen of interest (the protein or polypeptide or immunogenic conjugates of the invention) either in vivo or in vitro. The antibody-secreting lymphocytes are then fused with myeloma cells or transformed cells, which are capable of replicating indefinitely in cell culture. The resulting fused cells, or hybridomas, are immortal, immunoglobulin-secreting cell lines that can be cultured in vitro. Upon culturing the hybridomas, the resulting colonies can be screened for the production of desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, *Nature* 256:495 (1975), which is hereby incorporated by reference in its entirety.

Mammalian lymphocytes are immunized by in vivo immunization of the animal (e.g., a mouse, rat, rabbit, or human) with the protein or polypeptide or immunogenic conjugates of the invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described. Human hybridomas can be prepared using the EBV-hybridoma technique monoclonal antibodies (Cole et al., in *Monoclonal Antibodies and Cancer Therapy*, Alan R. Liss, Inc., pp. 77-96 (1985), which is hereby incorporated by reference in its entirety). Human antibodies may be used and can be obtained by using human hybridomas (Cote et al., *Proc. Natl. Acad. Sci. USA* 80:2026-2030 (1983), which is hereby incorporated by reference in its entirety) or by transforming human B cells with EBV virus in vitro (Cole et al., in *Monoclonal Antibodies and Cancer Therapy*, Alan R. Liss, Inc., pp. 77-96 (1985), which is hereby incorporated by reference in its entirety). In addition, monoclonal antibodies can be produced in germ-free animals (see PCT/US90/02545, which is hereby incorporated by reference in its entirety).

Procedures for raising polyclonal antibodies are also well known. Typically, such antibodies can be raised by administering the antigen (the protein or polypeptide or immunogenic conjugates of the invention) subcutaneously to rabbits, mice, or rats which have first been bled to obtain preimmune serum. The antigens can be injected as tolerated. Each injected material can contain adjuvants and the selected antigen (preferably in substantially pure or isolated form). Suitable adjuvants include, without limitation, Freund's complete or incomplete mineral gels such as aluminum hydroxide, surface active substances such as lysolecithin, pluronic polyols, polyanions, peptides, oil emulsions, dinitrophenol, and potentially useful human adjuvants such as bacille Calmette-Guerin and *Carynebacterium parvum*. The subject mammals are then bled one to two weeks after the first injection and periodically boosted with the same antigen (e.g., three times every six weeks). A sample of serum is then collected one to two weeks after each boost. Polyclonal antibodies can be recovered from the serum by affinity chromatography using the corresponding antigen to capture the antibody. This and other procedures for raising polyclonal antibodies are disclosed in Harlow & Lane, editors, *Antibodies: A Laboratory Manual* (1988), which is hereby incorporated by reference in its entirety.

In addition, techniques developed for the production of chimeric antibodies (Morrison et al., *Proc. Natl. Acad. Sci. USA* 81:6851-6855 (1984); Neuberger et al., *Nature* 312:604-608 (1984); Takeda et al., *Nature* 314:452-454 (1985), each of which is hereby incorporated by reference in its entirety) by splicing the genes from a mouse antibody molecule of appropriate antigen specificity together with genes from a human antibody molecule of appropriate biological activity can be used. For example, the genes from a mouse antibody molecule specific for epitopes in *Pneumocystis* A12 protein or polypeptide of the present invention can be spliced together with genes from a human antibody molecule of appropriate biological activity. A chimeric antibody is a molecule in which different portions are derived from different animal species, such as those having a variable region derived from a murine mAb and a human immunoglobulin constant region (e.g., U.S. Pat. No. 4,816,567 to Cabilly et al., and U.S. Pat. No. 4,816,397 to Boss et al., each of which is hereby incorporated by reference in its entirety).

In addition, techniques have been developed for the production of humanized antibodies (e.g., U.S. Pat. No. 5,585,089 to Queen, and U.S. Pat. No. 5,225,539 to Winter, each of which is hereby incorporated by reference in its entirety). An immunoglobulin light or heavy chain variable region consists of a "framework" region interrupted by three hypervariable regions, referred to as complementarity determining regions (CDRs). The extent of the framework region and CDRs have been precisely defined (see Kabat et al., "Sequences of Proteins of Immunological Interest," U.S. Department of Health and Human Services (1983), which is hereby incorporated by reference in its entirety). Briefly, humanized antibodies are antibody molecules from non-human species having one or more CDRs from the non-human species and a framework region from a human immunoglobulin molecule.

Alternatively, techniques described for the production of single chain antibodies (e.g., U.S. Pat. No. 4,946,778 to Ladner et al.; Bird, Science 242:423-426 (1988); Huston et al., Proc. Natl. Acad. Sci. USA 85:5879-5883 (1988); Ward et al., Nature 334:544-546 (1989), each of which is hereby incorporated by reference in its entirety) can be adapted to produce single chain antibodies against Pneumocystis A12 protein or polypeptide of the present invention. Single chain antibodies are formed by linking the heavy and light chain fragments of the Fv region via an amino acid bridge, resulting in a single chain polypeptide.

In addition to utilizing whole antibodies, the present invention also encompasses use of binding portions of such antibodies. Such binding portions include Fab fragments, F(ab')$_2$ fragments, and Fv fragments. These antibody fragments can be made by conventional procedures, such as proteolytic fragmentation procedures, as described in Goding, Monoclonal Antibodies: Principles and Practice, Academic Press (New York), pp. 98-118 (1983), which is hereby incorporated by reference in its entirety. Alternatively, the Fab fragments can be generated by treating the antibody molecule with papain and a reducing agent. Alternatively, Fab expression libraries may be constructed (Huse et al., Science 246:1275-1281 (1989), which is hereby incorporated by reference in its entirety) to allow rapid and easy identification of monoclonal Fab fragments with the desired specificity.

Antibodies of the present invention may be isolated by standard techniques known in the art, such as immunoaffinity chromatography, centrifugation, precipitation, etc. The antibodies (or fragments or variants thereof) are preferably prepared in a substantially purified form (i.e., at least about 85% pure, more preferably 90% pure, even more preferably at least about 95% to 99% pure).

From the foregoing, it should be appreciated that the present invention also relates to the isolated immune sera containing the polyclonal antibodies, compositions containing monoclonal antibodies, or fragments or variants thereof.

In addition, the antibodies generated by the vaccine formulations of the present invention can also be used in the production of anti-idiotypic antibody. The anti-idiotypic antibody can then in turn be used for immunization, in order to produce a subpopulation of antibodies that bind the initial antigen of the pathogenic microorganism, e.g., epitopes on Pneumocystis A12 protein or polypeptide of the present invention (Jeme, Ann. Immunol. (Paris) 125c:373 (1974); Jerne et al., EMBO J. 1:234 (1982), each of which is hereby incorporated by reference in its entirety).

Another type of active agent is an expression vector encoding an immunogenic protein or polypeptide (or fusion protein) of the present invention, which expression vector can be used for in vivo expression of the protein or polypeptide in eukaryotic, preferably mammalian, organisms. Hence, this aspect relates to a DNA vaccine.

DNA inoculation represents a relatively new approach to vaccine and immune therapeutic development. The direct injection of gene expression cassettes (i.e., as plasmids) into a living host transforms a number of cells into factories for production of the introduced gene products. Expression of these delivered genes has important immunological consequences and can result in the specific immune activation of the host against the novel expressed antigens. This approach to immunization can overcome deficits of traditional antigen-based approaches and provide safe and effective prophylactic and therapeutic vaccines. The transfected host cells can express and present the antigens to the immune system (i.e., by displaying fragments of the antigens on their cell surfaces together with class I or class II major hisotcompatibility complexes). DNA vaccines recently have been shown to be a promising approach for immunization against a variety of infectious diseases (Michel et al., "DNA-Mediated Immunization to the Hepatitis B Surface Antigen in Mice: Aspects of the Humoral Response Mimic Hepatitis B Viral Infection in Humans," Proc. Nat'l Acad. Sci. USA 92:5307-5311 (1995), which is hereby incorporated by reference in its entirety). Delivery of naked DNAs containing microbial antigen genes can induce antigen-specific immune responses in the host. The induction of antigen-specific immune responses using DNA-based vaccines has shown some promising effects (Wolff et al., "Long-Term Persistence of Plasmid DNA and Foreign Gene Expression in Mouse Muscle," Hum. Mol. Genet. 1:363-369 (1992), which is hereby incorporated by reference in its entirety).

The DNA vaccine can also be administered together with a protein-based vaccine, either as a single formulation or two simultaneously introduced formulations. See WO 2008/082719 to Rose et al., which is hereby incorporated by reference in its entirety.

According to one approach, the expression vector (to be used as a DNA vaccine) is a plasmid containing a DNA construct encoding the Pneumocystis A12 protein or polypeptide of the present invention. The plasmid DNA can be introduced into the organism to be exposed to the DNA vaccine, preferably via intramuscular or dermal injection, which plasmid DNA can be taken up by muscle or dermal cells for expression of the Pneumocystis A12 protein or polypeptide of the present invention.

According to another approach, the expression vector (to be used as a DNA vaccine) is an infective transformation vector, such as a viral vector.

When an infective transformation vector is employed to express a Pneumocystis A12 protein or polypeptide of the present invention in a host organism's cell, conventional recombinant techniques can be employed to prepare a DNA construct that encodes the protein or polypeptide and ligate the same into the infective transformation vector (Sambrook et al., Molecular Cloning: A Laboratory Manual, Second Edition, Cold Spring Harbor Press, NY (1989), which is hereby incorporated by reference in its entirety). The infective transformation vector so prepared can be maintained ex vivo in appropriate host cell lines, which may include bacteria, yeast, mammalian cells, insect cells, plant cells, etc. For example, having identified the protein or polypeptide to be expressed in cells of a host organism, a DNA molecule that encodes the oligoRNA can be ligated to appropriate 5' promoter regions and 3' transcription termination regions as discussed above, forming a DNA construct, so that the protein or polypeptide will be appropriately expressed in transformed cells. The selection of appropriate 5' promoters and 3' transcription termination regions is well known in the art and can be performed with routine skill. Suitable promoters for use in mammalian cells include those identified above.

Any suitable viral vector can be utilized to express the *Pneumocystis* A12 protein or polypeptide of the present invention. When transforming mammalian cells for heterologous expression of a *Pneumocystis* A12 protein or polypeptide of the present invention, exemplary viral vectors include adenovirus vectors, adeno-associated vectors, and retroviral vectors. Other suitable viral vectors now known or hereafter developed can also be utilized to deliver into cells a DNA construct encoding a protein or polypeptide of the present invention.

Adenovirus gene delivery vehicles can be readily prepared and utilized given the disclosure provided in Berkner, *Biotechniques* 6:616-627 (1988) and Rosenfeld et al., *Science* 252:431-434 (1991), WO 93/07283, WO 93/06223, and WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a DNA construct encoding a *Pneumocystis* A12 protein or polypeptide of the present invention. The use of adeno-associated viral gene delivery vehicles in vitro is described in Chatterjee et al., *Science* 258:1485-1488 (1992); Walsh et al., *Proc. Nat'l Acad. Sci. USA* 89:7257-7261 (1992); Walsh et al., *J. Clin. Invest.* 94:1440-1448 (1994); Flotte et al., *J. Biol. Chem.* 268:3781-3790 (1993); Ponnazhagan et al., *J. Exp. Med.* 179:733-738 (1994); Miller et al., *Proc. Nat'l Acad. Sci. USA* 91:10183-10187 (1994); Einerhand et al., *Gene Ther.* 2:336-343 (1995); Luo et al., *Exp. Hematol.* 23:1261-1267 (1995); and Zhou et al., *Gene Ther.* 3:223-229 (1996), each of which is hereby incorporated by reference in its entirety. In vivo use of these vehicles is described in Flotte et al., *Proc. Nat'l Acad. Sci. USA* 90:10613-10617 (1993); and Kaplitt et al., *Nature Genet.* 8:148-153 (1994), each of which is hereby incorporated by reference in its entirety.

Retroviral vectors which have been modified to form infective transformation systems can also be used to deliver into cells a DNA construct encoding a *Pneumocystis* A12 protein or polypeptide of the present invention. One such type of retroviral vector is disclosed in U.S. Pat. No. 5,849,586 to Kriegler et al., which is hereby incorporated by reference in its entirety.

Alternatively, a colloidal dispersion system can be used to deliver the DNA vaccine to the organism. Colloidal dispersion systems include macromolecule complexes, nanocapsules, microspheres, beads, and lipid-based systems including oil-in-water emulsions, micelles, mixed micelles, and liposomes. In one embodiment, the colloidal system is a lipid preparation including unilamaller and multilamellar liposomes.

Liposomes are artificial membrane vesicles that are useful as delivery vehicles in vitro and in vivo. It has been shown that large unilamellar vesicles (LUV), which range in size from about 0.2 to about 4.0 μm, can encapsulate a substantial percentage of an aqueous buffer containing DNA molecules (Fraley et al., *Trends Biochem. Sci.* 6:77 (1981), which is hereby incorporated by reference in its entirety). In addition to mammalian cells, liposomes have been used for delivery of polynucleotides in yeast and bacterial cells. For a liposome to be an efficient transfer vehicle, the following characteristics should be present: (1) encapsulation of the DNA molecules at high efficiency while not compromising their biological activity; (2) substantial binding to host organism cells; (3) delivery of the aqueous contents of the vesicle to the cell cytoplasm at high efficiency; and (4) accurate and effective expression of genetic information (Mannino et al., *Biotechniques* 6:682 (1988), which is hereby incorporated by reference in its entirety). In addition to such LUV structures, multilamellar and small unilamellar lipid preparations, which incorporate various cationic lipid amphiphiles can also be mixed with anionic DNA molecules to form liposomes (Feigner et al., *Proc. Natl. Acad. Sci. USA* 84(21): 7413 (1987), which is hereby incorporated by reference in its entirety).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and typically the presence of divalent cations. The appropriate composition and preparation of cationic lipid amphiphile:DNA formulations are known to those skilled in the art, and a number of references which provide this information are available (e.g., Bennett et al., *J. Liposome Research* 6(3):545 (1996), which is hereby incorporated by reference in its entirety).

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine, and distearoylphosphatidylcholine. Examples of cationic amphiphilic lipids useful in formulation of nucleolipid particles for polynucleotide delivery include the monovalent lipids N-[1-(2,3-dioleoyloxy)propyl]-N,N,N-trimethyl ammonium methyl-sulfate, N-[2,3-dioleoyloxy)propyl]-N,N,N-trimethyl ammonium chloride, and DC-cholesterol, the polyvalent lipids LipofectAMINE™, dioctadecylamidoglycyl spermine, Transfectam®, and other amphiphilic polyamines. These agents may be prepared with helper lipids such as dioleoyl phosphatidyl ethanolamine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization. The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

A further alternative for delivery of DNA is the use of a polymeric matrix which can provide either rapid or sustained release of the DNA vaccine to the organism. A number of polymeric matrices are known in the art and can be optimized with no more than routine skill.

A further aspect of the present invention relates to a pharmaceutical composition comprising (i) any of the isolated *Pneumocystis* A12 protein or polypeptide of the present invention, (ii) an immunogenic conjugate of the present invention covalently or non-covalently bonded to a carrier molecule, or (iii) an antibody of the present invention; and a pharmaceutically acceptable carrier.

The pharmaceutical compositions can include, but are not limited to, pharmaceutically suitable adjuvants, carriers, excipients, or stabilizers (collectively referred hereinafter as "carrier"). The pharmaceutical compositions are preferably, though not necessarily, in liquid form such as solutions, suspensions, or emulsions. Typically, the composition will contain from about 0.01 to 99 percent, preferably from about 20 to 75 percent of one or more of the above-listed active agents, together with the adjuvants, carriers, excipients, stabilizers, etc.

The pharmaceutical compositions of the present invention can take any of a variety of known forms that are suitable for a particular mode of administration. Exemplary modes of administration include, without limitation, orally, by inhalation, by intranasal instillation, topically, transdermally, parenterally, subcutaneously, intravenous injection, intra-arterial injection, intramuscular injection, intraplurally, intraperitoneally, by intracavitary or intravesical instillation, intraocularly, intraventricularly, intralesionally, intraspinally, or by application to mucous membranes, such as, that of the nose, throat, and bronchial tubes. Of these routes, intravenous and intraarterial administration are preferred.

The pharmaceutical forms suitable for injectable use (e.g., intravenous, intra-arterial, intramuscular, etc.) include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Oral dosage formulations can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; and sweetening agents such as sucrose, lactose, or saccharine; and flavoring agents such as peppermint oil, oil of wintergreen, or artificial flavorings. Generally, the ingredients are supplied either separately or mixed together in unit dosage form, for example, as a dry lyophilized powder or water free concentrate in a hermetically sealed container such as an ampule or sachette indicating the quantity of active agent.

For use as aerosols, the active agents in solution or suspension may be packaged in a pressurized aerosol container together with suitable propellants, for example, hydrocarbon propellants like propane, butane, or isobutane with conventional adjuvants. The active agents of the present invention also may be administered in a non-pressurized form such as in a nebulizer or atomizer.

For parenteral administration, aqueous solutions in water-soluble form can be used to deliver one or more of the active agents. Additionally, suspensions of the active agent(s) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

In addition to the formulations described previously, the active agent(s) may also be formulated as a depot preparation. Such long acting formulations may be administered by implantation (for example subcutaneously or intramuscularly) or by intramuscular injection. Thus, for example, the active agent(s) may be formulated with suitable polymeric or hydrophobic materials (e.g., as an emulsion in an acceptable oil) or ion exchange resins, or as sparingly soluble derivatives (e.g., as a sparingly soluble salt). Selection of polymeric matrix material is based on biocompatibility, biodegradability, mechanical properties, cosmetic appearance, and interface properties. The particular application of the active agent(s) will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate, as well as other materials that are known in the drug delivery arts. The bioceramics may be altered in composition, such as in calcium-aluminate-phosphate and processing to alter pore size, particle size, particle shape, and biodegradability.

The above-identified active agents are to be administered in an amount effective to achieve their intended purpose (i.e., to induce an active immune response or provide passive immunity). While individual needs vary, determination of optimal ranges of effective amounts of each component is within the skill of the art. The quantity administered will vary depending on the patient and the mode of administration and can be any effective amount. Typical dosages include about 0.1 to about 100 mg/kg·body wt. The preferred dosages include about 1 to about 50 mg/kg·body wt. However, because patients respond differently to therapies, monitoring of the treatment efficacy should be conducted, allowing for adjustment of the dosages as needed. Treatment regimen for the administration of the above-identified active agents of the present invention can also be determined readily by those with ordinary skill in art.

It is believed that the *Pneumocystis* A12 protein or polypeptide of the present invention can be used to induce active immunity against *Pneumocystis*. Thus, another aspect of the present invention relates to a vaccine comprising any of the isolated *Pneumocystis* A12 protein or polypeptide of the present invention.

A further aspect of the present invention relates to a method of immunizing a subject against infection of *Pneumocystis*. This method involves administering the vaccine of the present invention to a subject under conditions effective to immunize the subject against infection of *Pneumocystis*.

The subject administered the vaccine may further be administered a booster of the vaccine under conditions effective to enhance immunization of the subject.

A vaccine of the present invention can be administered to a subject orally, parenterally, for example, subcutaneously, intravenously, intramuscularly, intraperitoneally, by intranasal instillation, or by application to mucous membranes, such as, that of the nose, throat, and bronchial tubes. The vaccine or antidote may be administered alone or with suitable pharmaceutical carriers, and can be in solid or liquid form such as, tablets, capsules, powders, solutions, suspensions, or emulsions.

Another aspect of the present invention relates to treating or preventing infection in a subject by these organisms. The treatment or prevention of infection by these organisms can be carried out by administering to the subject an amount of one or more (even two or more) active agents described above (e.g., an isolated protein or polypeptide, an immunogenic conjugate, a DNA vaccine, or pharmaceutical compositions containing the same), where the amount is effective to induce an immune response in the subject and thereby treat or prevent infection of the subject by these organisms.

The use of active immunization in the immunocompromised host would seem counter intuitive. However, the use of vaccines in immunocompromised humans has been extensively reviewed by Pirofski and Casadevall ("Use of Licensed Vaccines for Active Immunization of the Immunocompromised Host," Clin. *Microbiol. Rev.* 11(1):1-26 (1998), which is hereby incorporated by reference in its entirety). Clinical trials have demonstrated the immunogenicity of *H. influenzae* vaccines in children with cancer and sickle cell disease (Feldman et al., "Risk of *Haemophilus influenzae* Type b Disease in Children with Cancer and Response of Immunocompromised Leukemic Children to a Conjugate Vaccine," *J. Infect. Dis.* 161(5):926-931 (1990); Shenep et al., "Response of Immunocompromised Children with Solid Tumors to a Conjugate Vaccine for *Haemophilus influenzae* Type b," *J. Pediatr.* 125(4):581-584 (1994); Gigliotti et al., "Immunization of Young Infants with Sickle Cell Disease with a *Haemophilus influenzae* Type b Saccharide-Diphtheria CRM197 Protein Conjugate Vaccine," *J. Pediatr.* 114(6): 1006-10 (1989); Gigliotti et al., "Serologic Follow-up of Children With Sickle Cell Disease Immunized with a *Haemophilus influenzae* Type b Conjugate Vaccine During Early Infancy," *J. Pediatr.* 118(6):917-919 (1991), each of which is hereby incorporated by reference in its entirety). New developments in vaccine technology should enhance the ability to vaccinate at-risk hosts.

In each of the embodiments that involves the induction of active immunity, immunostimulants may be co-administered to increase the immunological response. The term "immunostimulant" is intended to encompass any compound or composition which has the ability to enhance the activity of the immune system, whether it be a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin and pluronic polyols; polyanions; peptides; oil emulsions; alum; and MDP. Methods of utilizing these materials are known in the art, and it is well within the ability of the skilled artisan to determine an optimum amount of immunostimulant for a given active vaccine. More than one immunostimulant may be used in a given formulation. The immunogen may also be incorporated into liposomes, or conjugated to polysaccharides and/or other polymers for use in a vaccine formulation.

The treatment or prevention of infection by these organisms can be carried out by administering to a patient an amount of an antibody of the present invention (i.e., recognize the isolated protein or polypeptides or the immunogenic conjugates of the present invention), or previously identified antibodies that recognize the epitope shared by *Pneumocystis* A12 protein or polypeptide, where such antibodies are administered in an amount that is effective to treat or prevent infection by a *Pneumocystis* organism.

Passive immunotherapy with antibody preparations have been used successfully in many infectious diseases. Because of the immunocompromised host's altered ability to respond to active immunization, passive immunotherapy is a way to provide the benefit of antibody without the necessity of a specific immune response in the recipient. While often used to prevent diseases, e.g., varicella immune globulin in the compromised host, it can be used therapeutically. The use of immunoglobulin has been shown to improve the outcome of CMV disease, particularly pneumonitis, and enteroviral encephalitis, in the immunocompromised human host (Ljungman, "Cytomegalovirus Pneumonia: Presentation, Diagnosis, and Treatment," *Semin. Respir. Infect.* 10(4):209-215 (1995); Dwyer et al., "Intraventricular Gamma-globulin for the Management of Enterovirus Encephalitis," *Pediatr. Infect. Dis. J.* 7(5 Suppl):S30-3 (1988), each of which is hereby incorporated by reference in its entirety). Animal models support this approach in a variety of fungal infections (Casadevall et al., "Return to the Past: The Case for Antibody-based Therapies in Infectious Diseases," *Clin. Infect. Dis.* 21(1):150-161 (1995), which is hereby incorporated by reference in its entirety).

According to one therapeutic embodiment, the antibody to be administered is an antibody raised against a *Pneumocystis* A12 protein or polypeptide of the present invention.

According to another therapeutic embodiment, the antibody to be administered is an antibody raised against an immunogenic conjugate of the present invention.

In accordance with each of the above-identified methods of treating or preventing infection in a subject, the subject to be treated is preferably a mammal. Exemplary mammals to be treated include, without limitation, humans, horses, cows, pigs, orangutans, monkeys, rabbits, rats, or mice.

Regardless of the method of the present invention to be employed, i.e., either passive or active immunity, the immunopotency of a composition can be determined by monitoring the immune response of test animals following their immunization with the composition. Monitoring of the immune response can be conducted using any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

The immune response of the test subjects can be analyzed by various approaches such as: the reactivity of the resultant immune serum to the immunogenic conjugate or *Pneumocystis* A12 protein or polypeptide, as assayed by known techniques, e.g., enzyme linked immunosorbent assay ("ELISA"), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the patient), etc. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

After vaccination of an animal using the methods and compositions of the present invention, any binding assay known in the art can be used to assess the binding between the resulting antibody and the particular molecule. These assays may also be performed to select antibodies that exhibit a higher affinity or specificity for the particular antigen.

The antibodies or binding portions of the present invention are also useful for detecting in a sample the presence of epitopes of *Pneumocystis* A12 protein or polypeptide of the present invention and, therefore, the presence of either proteins containing the epitopes of *Pneumocystis* A12 protein or polypeptide, as well as *Pneumocystis*. This detection method includes the steps of providing an isolated antibody or binding portion thereof raised against an epitope containing *Pneumocystis* A12 protein or polypeptide of the present invention, adding to the isolated antibody or binding portion thereof a sample suspected of containing a quantity of *Pneumocystis* A12 protein or polypeptide or whole *Pneumocystis*, and then detecting the presence of a complex comprising the isolated antibody or binding portion thereof bound to the epitope (or protein or polypeptide or whole organism, as noted above).

Immunoglobulins, particularly antibodies (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one embodiment, an antibody of the invention that immunospecifically binds to an infectious disease agent, such as *Pneumocystis*, or *Pneumocystis* A12 protein or polypeptide may be used to diagnose, prognose or screen for the infectious disease.

Examples of suitable assays to detect the presence of the epitope include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

The tissue or cell type to be analyzed will generally include those which are known, or suspected, to express the particular epitope. The protein isolation methods employed herein may, for example, be such as those described in Harlow and Lane (*Antibodies: A Laboratory Manual*, Cold Spring Harbor Laboratory Press, Cold Spring Harbor, N.Y. (1988), which is hereby incorporated by reference in its entirety). The isolated cells can be derived from cell culture or from a subject. The antibodies (or functionally active fragments thereof) useful in the present invention may, additionally, be employed histologically, as in immunofluorescence, immunohistochemistry, or immunoelectron microscopy, for in situ detection of the epitope or pathogens expressing the epitope. In situ detection may be accomplished by removing a histological specimen from a patient, such as paraffin embedded sections of affected tissues and applying thereto a labeled antibody of the present invention. The antibody (or functionally active fragment thereof) is preferably applied by overlaying the labeled antibody onto a biological sample. If the molecule to which the antibody binds is present in the cytoplasm, it may be desirable to introduce the antibody inside the cell, for example, by making the cell membrane permeable. Through the use of such a procedure, it is possible to determine not only the presence of the particular molecule, but also its distribution in the examined tissue. Using the present invention, those of ordinary skill will readily perceive that any of a wide variety of histological methods (such as staining procedures) can be modified in order to achieve such in situ detection of epitopes of *Pneumocystis* A12 protein or polypeptide.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The biological sample may be brought in contact with and immobilized onto a solid phase support or carrier such as nitrocellulose, or other solid support which is capable of immobilizing cells, cell particles, or soluble proteins. The support may then be washed with suitable buffers followed by treatment with the detectably labeled antibody. The solid phase support may then be washed with the buffer a second time to remove unbound antibody. The amount of bound label on solid support may then be detected by conventional means. "Solid phase support or carrier" includes any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given antibody may be determined according to well known methods. Those skilled in the art will be able to determine operative and optimal assay conditions for each determination by employing routine experimentation.

One of the ways in which an antibody can be detectably labeled is by linking the same to an enzyme and use in an enzyme immunoassay (EIA) (Voller, "The Enzyme Linked Immunosorbent Assay (ELISA)," *Diagnostic Horizons* 2:1-7, Microbiological Associates Quarterly Publication, Walkersville, Md. (1978); Voller et al., *J. Clin. Pathol.* 31:507-520 (1978); Butler, *Meth. Enzymol.* 73:482-523 (1981); Maggio, E. (ed.), *Enzyme Immunoassay*, CRC Press, Boca Raton, Fla. (1980); Ishikawa et al., (eds.), *Enzyme immunoassay*, Kgaku Shoin, Tokyo (1981), each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric, or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or fragments, it is possible to detect the protein that the antibody was designed for through the use of a radioimmunoassay (RIA) (see, e.g., Weintraub, *Principles of Radioimmunoassays*, Seventh Training Course on Radioligand Assay Techniques, The Endocrine Society (1986), each of which is hereby incorporated by reference). The radioactive isotope can be detected by such means as the use of a gamma counter or a scintillation counter or by autoradiography. It is also possible to label the antibody with a fluorescent compound or semiconductor nanocrystals. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. A number of various semiconductor nanocrystals (i.e., nanodots) can be selected. Chemiluminescent compounds can alternatively be coupled to the antibodies. The presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Likewise, a bioluminescent compound may be used to label the synthetic antibody of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

A further aspect of the present invention relates to a diagnostic kit comprising either an antibody raised against any of the *Pneumocystis* A12 protein or polypeptide of the present invention, an antibody raised against an immunogenic conjugate comprising any of said *Pneumocystis* A12 protein or polypeptide of the present invention, or both.

Kits for diagnostic use are provided that contain in one or more containers an anti-*Pneumocystis* A12 protein or polypeptide, antibody, and, optionally, a labeled binding partner to the antibody. Alternatively, the anti-*Pneumocystis* A12 protein or polypeptide antibody can be labeled (with a detectable marker, e.g., a chemiluminescent, enzymatic, fluorescent, or radioactive moiety). Accordingly, the present invention provides a diagnostic kit that includes an anti-*Pneumocystis* A12 protein or polypeptide antibody and a control immunoglobulin. In a specific embodiment, one of the foregoing compounds of the container can be detectably labeled. A kit can optionally further include in a container, for use as a standard or control, a predetermined amount of a protein or polypeptide that is recognized by the antibody of the kit.

EXAMPLES

The following examples are provided to illustrate embodiments of the present invention, but they are by no means intended to limit its scope.

Example 1

Expression of an Optimized Antigen of *Pneumocystis* for Evaluation as a Potential Vaccine Protein was generated according to the flow chart illustration of FIG. 1. PCR was used to amplify the A12$_{46-3297}$ segment for cloning from stock of pET14b:A12$_{full}$. Next, gel extract was used to purify the gene fragment and clone into PCR4 TOPO sequencing vector. The vector was transformed into One Shot TOP10' chemically competent *E. coli* cells. The pCR4 TOPO:$A12_{46\text{-}3297}$ was sequenced with M13 vector to ensure correct sequence. A12 was cut with XhoI endonuclease to create sticky ends for ligation into the pET14b expression vector. pET14b was transformed with insert into TOP10' chemically competent *E. coli* cells. pET14b:$A12_{46\text{-}3297}$ was transformed into expression strains of *E. coli*: BL21 (DE3) pLysS and Rosetta-gami (DE3) pLysS. To ensure correct insert with proper orientation, sequencing and restriction diagnosis was performed. Protein expression was induced using 1 mM IPTG at $0.8 \leq OD_{600} \leq 1.0$ for 2 hours. Proteins were detected on a western blot using anti-6 His antibody, 4F11 antibody, pooled sera from mice in FG510 Thio:N-terminal half-protein, and pooled sera from mice in FG510 *Pneumocystis* immunized.

Because expression of the full A12 protein was extremely limited due to codon bias (FIG. 2), A12 was instead cloned as two half-length proteins as shown in FIG. 3. The N-terminal half (shown in light shading) was expressed poorly, so was instead produced as a 500 amino acid peptide fused to thioredoxin. The C-terminal half (shown in dark shading) was expressed at high levels.

Mice were immunized subcutaneously with protein and TiterMax™. Mice were then injected with GK to CD4+ deplete. Mice were inoculated with *Pneumocystis* at a dose of 5e5. After 4 weeks, the presence of antibody and *Pneumocystis* burden was assessed in all treatments.

Example 2

Immunization Using an Optimized Antigen of *Pneumocystis*

Figure 5:
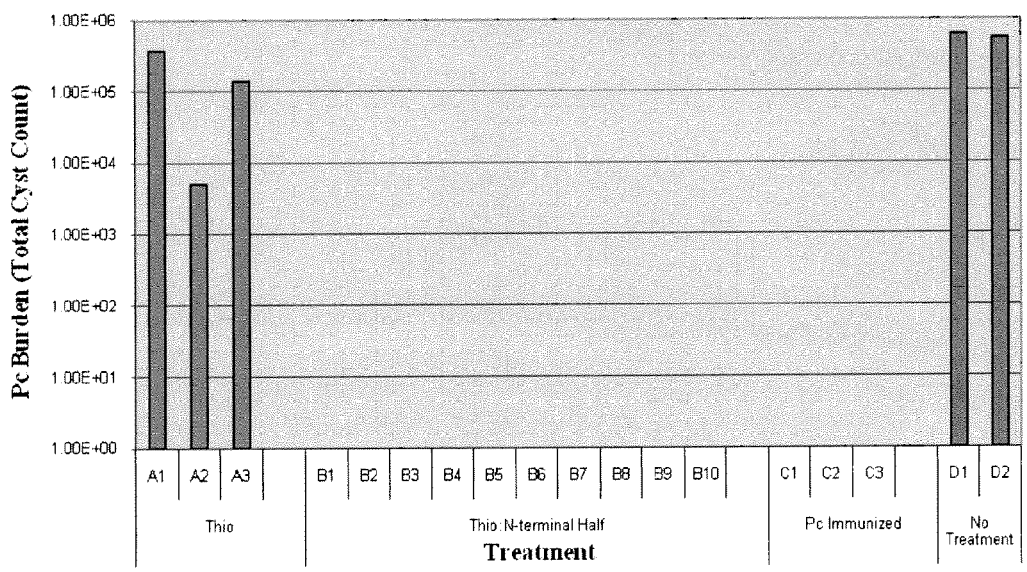
FIG. 5 is a graph showing results from FG510. Thio:N-terminal fusion protein provides significant protection and Thio alone provides only a slight reduction in burden.

Immunizations were performed on CB17 WT mice at Day 0 (FIG. 4) in study FG410 and FG510 (FIG. 5). Mice were CD4 depleted prior to *Pneumocystis* inoculation. In FG410, mice were *Pneumocystis* inoculated via intranasal inoculation. In FG510, mice were *Pneumocystis* inoculated by cohousing. Four weeks after challenge with *Pneumocystis*, mice were euthanized and lung homogenates and blood sera were taken to evaluate *Pneumocystis* burden and immune response, respectively.

Figure 6:
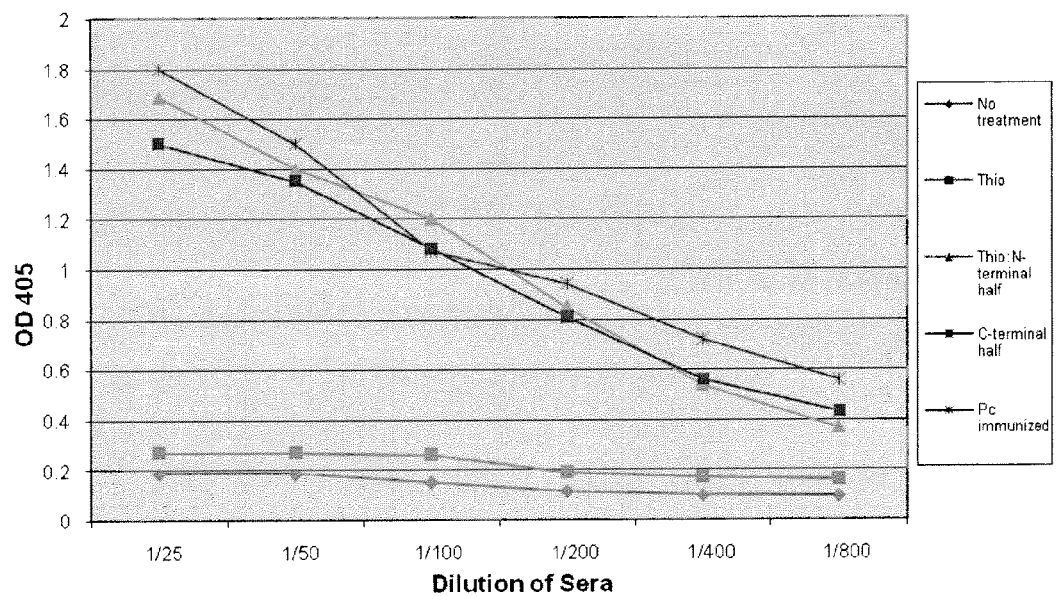
FIG. 6 is a graph showing *Pneumocystis* ELISA of grouped, pooled sera against lung homogenate of unaffected and affected CB17 WT mice. Sera from both Thio:C1 (i.e., thoiredoxin—N-terminal half of *Pneumocystis* A12) and B13 recognize *Pneumocystis* antigen in lung homogenate.

The N-terminal half generated as a thioredoxin fusion protein provided significant protection (FIG. 6), but was not recognized by 4F11 (FIG. 7). The C-terminal half-length protein was recognized by 4F11, but only provided a half log reduction in burden.

Figure 8:
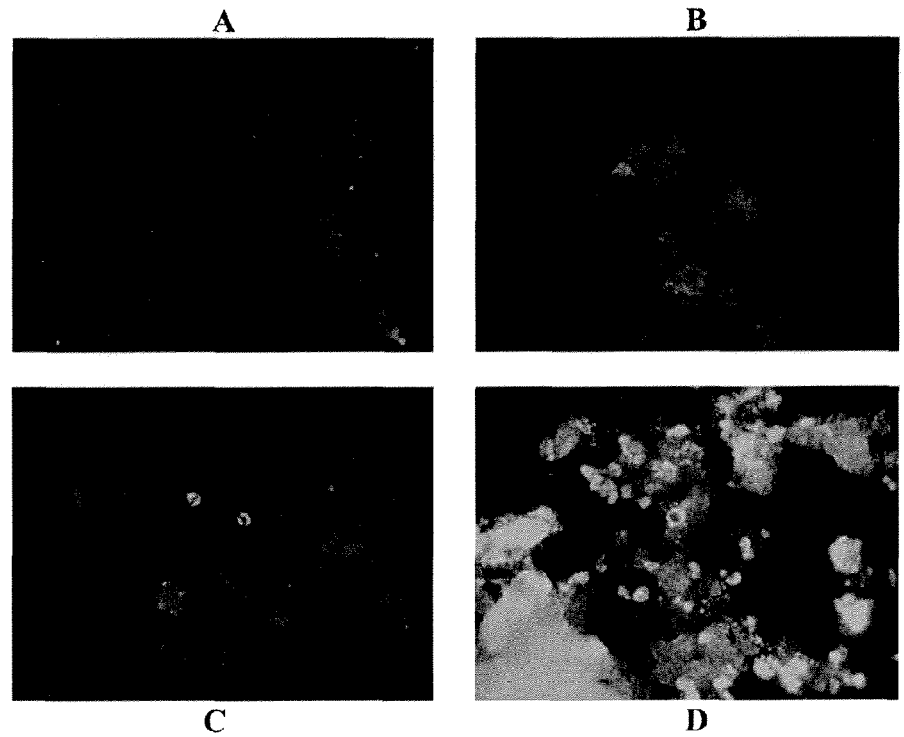
FIG. 8 is a table showing activity data, where "thio-c1" is the fusion protein (i.e., thoiredoxin—N-terminal half of *Pneumocystis* A12), "thio" is thioredoxin alone (− control), and Pc is *Pneumocystis* (+ control).
Figures 13, 14:
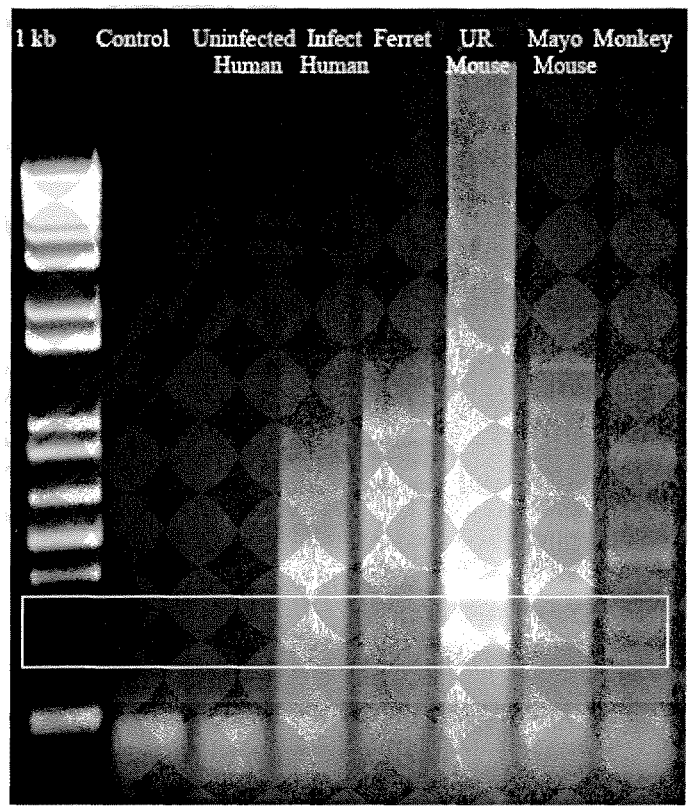
FIG. 13 shows PCR results on Uninfected Human vs. Pj Infected Human, Infected Ferret, Infected Mouse, and Infected Monkey with Primer Pair F3+R2. Proof that the primer pair is only amplifying a Pc/Pj specific region.
FIG. 14 shows Wakefield primers used to detect *Pneumocystis*. 19 archival samples known to be positive for *Pneumocystis* were re-tested with the Wakefield primers and only 10/19 yielded a + result (indicating potential degradation of the DNA). The F3/R2 degenerate primers were also tested to ensure primers were landing only on infected individuals and confirm conservation of the A12 target sequence in several human samples.
Figure 15:
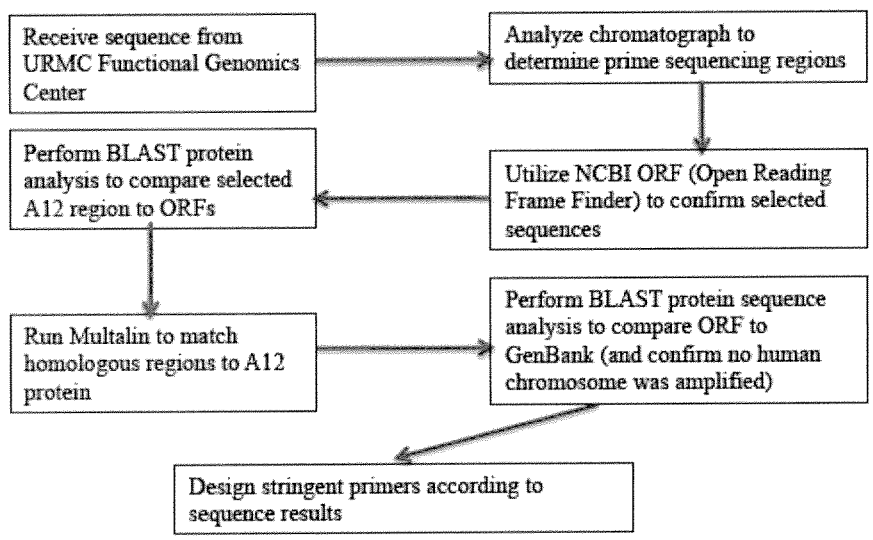
FIG. 15 shows a schematic of sequence analysis procedure to determine percent homology between A12 and amplified PCR product.

Additional activity data for thio-c1 is illustrated in the table of FIG. 8.

Clones were generated from a stock of pET14b:A12 using primers to eliminate the first 45 base pairs. PCR product was then cloned into TOPO vector for sequencing. From here, the insert was cut and ligated back into pET14b expression vector. The pET14b:A12$_{46-3297}$ plasmid was transformed into One Shot Top 10 competent cells, isolated, and then transformed into two expression strains: Rosetta-gami (DE3) pLysS and BL21 (DE3) pLysS. The cells were cultured, induced with IPTG for expression, and protein was extracted.

In conclusion, (i) A12 antigen has protective capabilities against *Pneumocystis* in mice; (ii) the N-terminal half of the protein provides significant protection, while the C-terminal half of the protein protects only slightly; and (iii) using Rosetta-gami (DE3) pLysS *E. coli* optimized for expression of toxic proteins enhances A12 protein expression.

Example 3

Identifying Homologues in Human *Pneumocystis jiroveci* to Regions of the A12 Protein from Mouse *Pneumocystis*

*Pneumocystis* is the fungal pathogen that results in *Pneumocystis carinii* pneumonia (PCP)—a hallmark lung infection and leading cause of death in patients with compromised immune systems. More than half of adults who have died from AIDS complications suffered at least 1 PCP infection.

Although *Pneumocystis* affecting each mammalian species is different, there exist homologous regions as confirmed by the monoclonal antibody (Mab) 4F11. This Mab was proven to bind to conserved regions between different species of *Pneumocystis* confirmed by immunofluorescence assays (IFA). Furthermore, this mouse *Pneumocystis* protein has been cloned and expressed and found to confer antibody production and protection to *Pneumocystis* infection in mice. The next step is to identify the human homologue, clone and express the protein, and confirm binding with 4F11 Mab to the human *Pneumocystis* protein. Immunization with this homologue may confer a protective antibody response, decreasing *Pneumocystis* burden, providing a potential vaccine strategy for therapy to PCP.

DNA was isolated from human *Pneumocystis jirovecii* ("Pj") infected lung homogenate. Human Pj DNA was amplified by Polymerase Chain Reaction (PCR) utilizing degenerate primers which align to A12 protein sequence. Gel extraction was performed and purified product was used to prepare for cloning. Product was purified and cloned into pCR 4-TOPO vector and transformed into OneShot TOP10 competent *E. coli* cells. Colonies were plated onto LB/KAN plates. Vectors with the insert will be able to survive as the vector confers resistance to kanamycin. Plasmid DNA was isolated and screened for insert utilizing EcoR1 digest and PCR. Sequencing reactions were performed with Reverse M13 and sent to URMC. Sequence analysis was conducted utilizing NCBI BLAST and Multalin programs.

Previous research indicates that active immunization against *Pneumocystis* (using the A12 protein) reduces *P. murina* burden in mice by 1 log. IFA analysis with 4F11 monoclonal antibody indicates there is a shared region of homology in the A12 protein between mouse and human *Pneumocystis*. Using the degenerate primer pair, Forward 3 and Reverse 2, a region of the human Pj A12 homologue was amplified and found to have a 43% query match and a 30% max identity to the mouse Pc A12 protein-confirming that there is a similar region in Human Pj. Primers more specific for the human Pj A12 gene designed by utilizing the sequence of the amplified human homologue. The stringent primer pairs designed for the next step are:

```
2SR2 (Reverse):
                                    (SEQ ID NO: 7)
5'-ATC TTC TTT GTA GCA TGG AAG TTG-3';

2SF3 (Forward):
                                    (SEQ ID NO: 8)
5'-GTG GCC TAT GGC AAC TTC CAG-3';

SKYVE (Forward):
                                    (SEQ ID NO: 9)
5'-CTA AAT ATG TAG AAA-3';

SKYVE (Reverse):
                                   (SEQ ID NO: 10)
5'-TTT CTA CAT ATT TAG-3'.
```

The next step is to utilize these specific primer pairs to perform nested PCR on the infected human Pj samples and amplify a larger portion of the region.

What is claimed is:

1. An isolated *Pneumocystis* A12 protein or polypeptide fragment comprising an amino acid sequence that is at least 90% identical to at least a 40 contiguous amino acid sequence of SEQ ID NO:2.

2. A vaccine comprising the isolated protein or polypeptide according to claim 1.

3. A pharmaceutical composition comprising:
   the isolated protein or polypeptide according to claim 1 and
   a pharmaceutically acceptable carrier.

4. A vaccine comprising a fusion protein comprising:
   a first protein or protein fragment comprising an N-terminal region of *Pneumocystis* A12 and
   a second protein or protein fragment linked to the first protein or protein fragment.

5. A pharmaceutical composition comprising:
   a fusion protein comprising:
      a first protein or protein fragment comprising an N-terminal region of *Pneumocystis* A12 and
      a second protein or protein fragment linked to the first protein or protein fragment and
   a pharmaceutically acceptable carrier.

* * * * *

SEQUENCE LISTING

```
<160> NUMBER OF SEQ ID NOS: 13

<210> SEQ ID NO 1
<211> LENGTH: 1101
<212> TYPE: PRT
<213> ORGANISM: artificial
```

-continued

```
<220> FEATURE:
<223> OTHER INFORMATION: Full-length amino acid sequence of the A12
      protein from mouse-derived Pneumocystis

<400> SEQUENCE: 1

Met Phe Phe Leu Arg Ile Ile Phe Ile Phe Phe Leu Lys Ile Ser
1               5                   10                  15

Tyr Ala Glu Asn Thr Asp Lys Leu Ser Asp Phe Glu Lys Lys Tyr Pro
            20                  25                  30

Glu Leu Tyr Gln Ala Asn Pro His Ala Leu Lys Leu Glu Ala Leu Lys
            35                  40                  45

Ser Gly Phe Ser Gly Lys Ser Val Lys Lys Gly Leu Gly Val Phe His
50                  55                  60

Ile Gly Asn Leu Gly His Tyr Arg Asp His Lys Pro Val Ile Leu His
65                  70                  75                  80

Val Ile Met Gly Leu Thr Val Gly Leu Ala Glu Cys Arg Gly Thr Leu
                85                  90                  95

Ala Glu Arg Cys Lys Val Ile Lys Ala Leu Gly Asn Pro Ile Thr Gln
            100                 105                 110

Tyr Cys Asn Lys Pro Tyr Asp Thr Cys Gln Asp Tyr Phe Asp Ala Arg
            115                 120                 125

Asn Tyr Leu Leu Pro Met Lys Asp Gln Leu Lys Asn Pro His Ala His
130                 135                 140

His Asp Ala Cys Arg Thr Ile Leu Leu Asn Cys Leu Phe Phe Lys His
145                 150                 155                 160

Arg Asn Tyr Ile Thr Ser Asp Cys Val Pro Leu Val Ala Leu Cys Tyr
                165                 170                 175

Leu Arg Val Arg Gln Asn Phe Val Glu Ala Ile Met Thr Glu Ala Leu
            180                 185                 190

Arg Gly Glu Ile Asn Thr Lys Gly Ala Ala Ala Met Lys Lys Val
            195                 200                 205

Cys Glu Lys Ile Gly His Glu Ser Pro Asp Leu Leu His Leu Cys Phe
210                 215                 220

Lys Thr Thr Val Leu Glu Lys Pro Lys Arg Ser Asn Lys Gln Tyr Ile
225                 230                 235                 240

Glu Asp Val Lys Ser Arg Ile Arg Thr Val Ser Thr Gly Asn Cys Arg
                245                 250                 255

Gln Val Leu Glu Glu Cys Tyr Phe Asn Val Leu Asp Tyr Pro Asp Ile
            260                 265                 270

Tyr Gln Ser Cys Arg Asn Phe Arg Arg Phe Cys Ser Glu Ile Gly Val
            275                 280                 285

Val Tyr Thr Pro Val Asp Ser Thr Phe Asp Leu Phe Gln Lys Pro Leu
            290                 295                 300

Ser Ala Glu Lys Leu Leu Ile Asp Thr Ser Ser Lys Ile Ser Glu Asp
305                 310                 315                 320

Leu Gly Leu Gly Phe Ser Lys Tyr Val Gln Lys Ser Ser Asn Leu
                325                 330                 335

Glu Ile Ala Ala Tyr Leu Val Asn Lys Thr Trp Val Tyr Asp Asn Asp
            340                 345                 350

Cys Arg Asn Lys Leu Lys Glu Leu Cys Leu His Ile Ala Ser Leu Pro
            355                 360                 365

Leu Thr Lys Gln Leu Cys Thr Leu Ala His Asp Arg Asn Ser Lys Leu
            370                 375                 380
```

```
Cys Arg Asp Phe Tyr Asn Ser Ile Gly Thr Glu Cys Tyr Ser Leu Tyr
385                 390                 395                 400

Tyr Glu Phe Lys Asn Val Gly Leu Leu Tyr Asn Tyr Thr Tyr Arg Leu
            405                 410                 415

Ser Arg Asp Gln Cys Ser Lys Tyr Val Glu Arg Cys Leu Phe Leu Arg
            420                 425                 430

Glu Gln Tyr Ala Tyr Trp Asn Ser Leu Asp Thr Cys Ala Asn Val Phe
            435                 440                 445

Ser Ser Cys Tyr Lys Glu Asp Met Asp Phe Ser Ala Lys Leu Asp Leu
            450                 455                 460

Leu Asn Arg Ile Lys Asp Lys Ile Val Val Pro Lys Gly Asn Thr Arg
465                 470                 475                 480

Tyr Phe Val Glu Leu Leu Cys Lys Ser Tyr Ile Val Ala Glu Cys Ser
            485                 490                 495

Ala Ser Asp Leu Met Phe Lys Ser Tyr Ala Leu Met Glu Ala Cys Leu
            500                 505                 510

His Pro Glu Arg Ile Cys Arg Glu Leu Lys Asn His Phe Ser Glu Glu
            515                 520                 525

Ser Arg Lys Leu Glu Asn Lys Leu Arg Ser Ile Leu Lys Pro Thr Tyr
530                 535                 540

Tyr Glu Cys Lys Asp Leu Gly Gln Lys Cys Asn Ser Gly Phe Tyr Phe
545                 550                 555                 560

Asp Gly Asp Ile Glu Ala Gln Cys Asn His Phe Lys Lys Arg Cys Gln
            565                 570                 575

Asp Lys Gln Glu Arg Leu Lys Leu Ile Asn His Ile Val Asp Ser Ser
            580                 585                 590

Ala Leu Tyr Leu Ala Asn Glu Val Gln Cys Arg Thr Tyr Phe Asp Ser
            595                 600                 605

Phe Cys Gly Ala Asn Val Lys Gln Glu Phe Lys Gln Ile Cys Asn Lys
            610                 615                 620

Gly Ala Asn Gly Ile Cys Pro Asp Ile Ile Asp Ser Lys Glu His
625                 630                 635                 640

Cys Ala His Leu Ile Asn His Leu Thr Ser Leu Gly Ile Ser Ser Ser
            645                 650                 655

Ser Ala Ser Leu Pro Leu Asp Tyr Cys Asp Ser Ala Ile Asn Tyr Cys
            660                 665                 670

Asn Ser Leu Ser Lys Phe Cys Thr Glu Ser Lys Arg Gln Cys Asp Ser
            675                 680                 685

Val Ile Ser Phe Cys Thr Ser Glu Ser Lys Lys Thr Asp Glu Tyr Gly
690                 695                 700

Ser Phe Ile Asp Gln Tyr Pro Ala Ala Ala Asn Ala Thr Lys Cys
705                 710                 715                 720

Lys Val Thr Leu Lys Glu Leu Cys Gln Asp Ser Ser Lys Lys Asp Ser
            725                 730                 735

Tyr Ser Thr Leu Cys Ala Tyr Asn Lys Asp Gly Tyr Thr Glu Ile Cys
            740                 745                 750

Lys Asn Leu Arg Asn Phe Ile Glu Lys Ala Cys Glu Asn Leu Arg Ile
            755                 760                 765

His Leu His Thr Tyr Asp Thr Asn Ser Leu Asn Thr Asn Lys Gly Ser
            770                 775                 780

Ala Gln Asp Arg Cys Thr Tyr Ile Arg Asn Leu Tyr Phe Lys Phe Lys
785                 790                 795                 800
```

```
Asn Ile Cys Leu Leu Val Asp Pro Phe Tyr Asp Leu Ser Pro Ile Ile
                805                 810                 815

Thr Gln Glu Cys Lys Thr Asn Ile Ser Glu Pro Ala Leu Pro Asp Lys
            820                 825                 830

Asp Pro Gln Pro Thr Ser Ser Pro Gln Pro Lys Pro Arg Pro Arg Pro
        835                 840                 845

Arg Pro Gln Pro Gln Pro His Pro His Pro Lys Pro Gln Pro Gln Pro
    850                 855                 860

Thr Pro Glu Pro Gln Pro Gln Pro Ala Pro Glu Pro Arg Pro Gln Pro
865                 870                 875                 880

Thr Ser Lys Pro Arg Pro Gln Pro Thr Ser Lys Pro Arg Pro Gln Pro
                885                 890                 895

Thr Pro Glu Pro Arg Pro Leu Pro Val Pro Gly Pro Gly Pro Leu Pro
            900                 905                 910

Val Pro Gly Pro Arg Pro Gln Pro Gln Pro Gln Pro Gln Pro Gln Pro
        915                 920                 925

Gln Pro Gln Pro Gln Pro Gln Pro Gln Pro Gln Pro Gln Pro Gln Pro
    930                 935                 940

Gln Pro Gln Pro Gln Pro Gln Pro Lys Pro Gln Pro Pro Ser Gln Ser
945                 950                 955                 960

Thr Ser Glu Ser Ala Ser Gln Ser Lys Pro Lys Pro Thr Thr Gln Thr
                965                 970                 975

Lys Pro Ser Pro Arg Pro His Pro Lys Pro Val Pro Lys Pro Ser Ser
                980                 985                 990

Ile Asp Thr Gly Pro Ser Lys Ser Asp Ser Ser Phe Ile Phe Thr Val
            995                 1000                1005

Thr Lys Thr Ile Thr Lys Ile Ser Glu Thr Glu Lys Pro Ser Thr
    1010            1015                1020

Lys Pro Ser Val Lys Pro Thr Ser Thr Lys Thr Thr Ser Lys Pro
    1025            1030                1035

Ser Thr Lys Pro Ser Thr Lys Pro Ser Val Lys Pro Ala Asn His
    1040            1045                1050

Ser Thr Lys Thr Thr Ser Glu Ser Glu Lys Pro Thr Leu Glu Glu
    1055            1060                1065

Val Pro Glu Thr Lys Gly Asn Gly Val Arg Val Ile Gly Phe Glu
    1070            1075                1080

Gly Leu Gln Leu Leu Ser Met Ile Val Ala Ile Ile Ile Gly Ile
    1085            1090                1095

Trp Ile Met
    1100

<210> SEQ ID NO 2
<211> LENGTH: 475
<212> TYPE: PRT
<213> ORGANISM: artificial
<220> FEATURE:
<223> OTHER INFORMATION: N-terminal portion of the A12 protein from
      mouse-derived Pneumocystis

<400> SEQUENCE: 2

Met Phe Phe Leu Arg Ile Ile Phe Ile Phe Leu Lys Ile Ser
1               5                   10                  15

Tyr Ala Glu Asn Thr Asp Lys Leu Ser Asp Phe Glu Lys Lys Tyr Pro
            20                  25                  30

Glu Leu Tyr Gln Ala Asn Pro His Ala Leu Lys Leu Glu Ala Leu Lys
        35                  40                  45
```

-continued

```
Ser Gly Phe Ser Gly Lys Ser Val Lys Lys Gly Leu Gly Val Phe His
    50                  55                  60
Ile Gly Asn Leu Gly His Tyr Arg Asp His Lys Pro Val Ile Leu His
65                  70                  75                  80
Val Ile Met Gly Leu Thr Val Gly Leu Ala Glu Cys Arg Gly Thr Leu
                85                  90                  95
Ala Glu Arg Cys Lys Val Ile Lys Ala Leu Gly Asn Pro Ile Thr Gln
            100                 105                 110
Tyr Cys Asn Lys Pro Tyr Asp Thr Cys Gln Asp Tyr Phe Asp Ala Arg
            115                 120                 125
Asn Tyr Leu Leu Pro Met Lys Asp Gln Leu Lys Asn Pro His Ala His
            130                 135                 140
His Asp Ala Cys Arg Thr Ile Leu Leu Asn Cys Leu Phe Phe Lys His
145                 150                 155                 160
Arg Asn Tyr Ile Thr Ser Asp Cys Val Pro Leu Val Ala Leu Cys Tyr
                165                 170                 175
Leu Arg Val Arg Gln Asn Phe Val Glu Ala Ile Met Thr Glu Ala Leu
            180                 185                 190
Arg Gly Glu Ile Asn Thr Lys Gly Ala Ala Ala Met Lys Lys Val
            195                 200                 205
Cys Glu Lys Ile Gly His Glu Ser Pro Asp Leu Leu His Leu Cys Phe
210                 215                 220
Lys Thr Thr Val Leu Glu Lys Pro Lys Arg Ser Asn Lys Gln Tyr Ile
225                 230                 235                 240
Glu Asp Val Lys Ser Arg Ile Arg Thr Val Ser Thr Gly Asn Cys Arg
                245                 250                 255
Gln Val Leu Glu Glu Cys Tyr Phe Asn Val Leu Asp Tyr Pro Asp Ile
            260                 265                 270
Tyr Gln Ser Cys Arg Asn Phe Arg Arg Phe Cys Ser Glu Ile Gly Val
            275                 280                 285
Val Tyr Thr Pro Val Asp Ser Thr Phe Asp Leu Phe Gln Lys Pro Leu
            290                 295                 300
Ser Ala Glu Lys Leu Leu Ile Asp Thr Ser Ser Lys Ile Ser Glu Asp
305                 310                 315                 320
Leu Gly Leu Gly Phe Ser Lys Tyr Val Gln Lys Ser Ser Asn Leu
                325                 330                 335
Glu Ile Ala Ala Tyr Leu Val Asn Lys Thr Trp Val Tyr Asp Asn Asp
            340                 345                 350
Cys Arg Asn Lys Leu Lys Glu Leu Cys Leu His Ile Ala Ser Leu Pro
            355                 360                 365
Leu Thr Lys Gln Leu Cys Thr Leu Ala His Asp Arg Asn Ser Lys Leu
            370                 375                 380
Cys Arg Asp Phe Tyr Asn Ser Ile Gly Thr Glu Cys Tyr Ser Leu Tyr
385                 390                 395                 400
Tyr Glu Phe Lys Asn Val Gly Leu Leu Tyr Asn Tyr Thr Tyr Arg Leu
                405                 410                 415
Ser Arg Asp Gln Cys Ser Lys Tyr Val Glu Arg Cys Leu Phe Leu Arg
            420                 425                 430
Glu Gln Tyr Ala Tyr Trp Asn Ser Leu Asp Thr Cys Ala Asn Val Phe
            435                 440                 445
```

```
Ser Ser Cys Tyr Lys Glu Asp Met Asp Phe Ser Ala Lys Leu Asp Leu
    450                 455                 460

Leu Asn Arg Ile Lys Asp Lys Ile Val Val Pro
465                 470                 475

<210> SEQ ID NO 3
<211> LENGTH: 579
<212> TYPE: PRT
<213> ORGANISM: artificial
<220> FEATURE:
<223> OTHER INFORMATION: C-terminal portion of the A12 protein from
      mouse-derived Pneumocystis

<400> SEQUENCE: 3

Asn His Phe Ser Glu Glu Ser Arg Lys Leu Glu Asn Lys Leu Arg Ser
1               5                   10                  15

Ile Leu Lys Pro Thr Tyr Tyr Glu Cys Lys Asp Leu Gly Gln Lys Cys
            20                  25                  30

Asn Ser Gly Phe Tyr Phe Asp Gly Asp Ile Glu Ala Gln Cys Asn His
        35                  40                  45

Phe Lys Lys Arg Cys Gln Asp Lys Gln Glu Arg Leu Lys Leu Ile Asn
    50                  55                  60

His Ile Val Asp Ser Ser Ala Leu Tyr Leu Ala Asn Glu Val Gln Cys
65                  70                  75                  80

Arg Thr Tyr Phe Asp Ser Phe Cys Gly Ala Asn Val Lys Gln Glu Phe
                85                  90                  95

Lys Gln Ile Cys Asn Lys Gly Ala Asn Gly Ile Cys Pro Asp Ile Ile
            100                 105                 110

Asp Asp Ser Lys Glu His Cys Ala His Leu Ile Asn His Leu Thr Ser
        115                 120                 125

Leu Gly Ile Ser Ser Ser Ala Ser Leu Pro Leu Asp Tyr Cys Asp
    130                 135                 140

Ser Ala Ile Asn Tyr Cys Asn Ser Leu Ser Lys Phe Cys Thr Glu Ser
145                 150                 155                 160

Lys Arg Gln Cys Asp Ser Val Ile Ser Phe Cys Thr Ser Glu Ser Lys
                165                 170                 175

Lys Thr Asp Glu Tyr Gly Ser Phe Ile Asp Gln Tyr Pro Ala Ala Ala
            180                 185                 190

Ala Asn Ala Thr Lys Cys Lys Val Thr Leu Lys Glu Leu Cys Gln Asp
        195                 200                 205

Ser Ser Lys Lys Asp Ser Tyr Ser Thr Leu Cys Ala Tyr Asn Lys Asp
    210                 215                 220

Gly Tyr Thr Glu Ile Cys Lys Asn Leu Arg Asn Phe Ile Glu Lys Ala
225                 230                 235                 240

Cys Glu Asn Leu Arg Ile His Leu His Thr Tyr Asp Thr Asn Ser Leu
                245                 250                 255

Asn Thr Asn Lys Gly Ser Ala Gln Asp Arg Cys Thr Tyr Ile Arg Asn
            260                 265                 270

Leu Tyr Phe Lys Phe Lys Asn Ile Cys Leu Leu Val Asp Pro Phe Tyr
        275                 280                 285

Asp Leu Ser Pro Ile Ile Thr Gln Glu Cys Lys Thr Asn Ile Ser Glu
    290                 295                 300

Pro Ala Leu Pro Asp Lys Asp Pro Gln Pro Thr Ser Ser Pro Gln Pro
305                 310                 315                 320

Lys Pro Arg Pro Arg Pro Arg Pro Gln Pro Gln Pro His Pro His Pro
                325                 330                 335
```

```
Lys Pro Gln Pro Gln Pro Thr Pro Glu Pro Gln Pro Ala Pro
            340                 345                 350

Glu Pro Arg Pro Gln Pro Thr Ser Lys Pro Arg Pro Gln Pro Thr Ser
            355                 360                 365

Lys Pro Arg Pro Gln Pro Thr Pro Glu Pro Arg Pro Leu Pro Val Pro
            370                 375                 380

Gly Pro Gly Pro Leu Pro Val Pro Gly Pro Arg Pro Gln Pro Gln Pro
385                 390                 395                 400

Gln Pro Gln Pro Gln Pro Gln Pro Gln Pro Gln Pro Gln Pro
            405                 410                 415

Gln Pro Gln Pro Gln Pro Gln Pro Gln Pro Gln Pro Lys Pro
            420                 425                 430

Gln Pro Pro Ser Gln Ser Thr Ser Glu Ser Ala Ser Gln Ser Lys Pro
            435                 440                 445

Lys Pro Thr Thr Gln Thr Lys Pro Ser Pro Arg Pro His Pro Lys Pro
            450                 455                 460

Val Pro Lys Pro Ser Ser Ile Asp Thr Gly Pro Ser Lys Ser Asp Ser
465                 470                 475                 480

Ser Phe Ile Phe Thr Val Thr Lys Thr Ile Thr Lys Ile Ser Glu Thr
            485                 490                 495

Glu Lys Pro Ser Thr Lys Pro Ser Val Lys Pro Thr Ser Thr Lys Thr
            500                 505                 510

Thr Ser Lys Pro Ser Thr Lys Pro Ser Thr Lys Pro Ser Val Lys Pro
            515                 520                 525

Ala Asn His Ser Thr Lys Thr Thr Ser Glu Ser Glu Lys Pro Thr Leu
            530                 535                 540

Glu Glu Val Pro Glu Thr Lys Gly Asn Gly Val Arg Val Ile Gly Phe
545                 550                 555                 560

Glu Gly Leu Gln Leu Leu Ser Met Ile Val Ala Ile Ile Gly Ile
            565                 570                 575

Trp Ile Met

<210> SEQ ID NO 4
<211> LENGTH: 1085
<212> TYPE: PRT
<213> ORGANISM: artificial
<220> FEATURE:
<223> OTHER INFORMATION: Pneumocystis A12 protein fragment

<400> SEQUENCE: 4

Tyr Ala Glu Asn Thr Asp Lys Leu Ser Asp Phe Glu Lys Lys Tyr Pro
1               5                   10                  15

Glu Leu Tyr Gln Ala Asn Pro His Ala Leu Lys Leu Glu Ala Leu Lys
            20                  25                  30

Ser Gly Phe Ser Gly Lys Ser Val Lys Lys Gly Leu Gly Val Phe His
            35                  40                  45

Ile Gly Asn Leu Gly His Tyr Arg Asp His Lys Pro Val Ile Leu His
        50                  55                  60

Val Ile Met Gly Leu Thr Val Gly Leu Ala Glu Cys Arg Gly Thr Leu
65                  70                  75                  80

Ala Glu Arg Cys Lys Val Ile Lys Ala Leu Gly Asn Pro Ile Thr Gln
            85                  90                  95

Tyr Cys Asn Lys Pro Tyr Asp Thr Cys Gln Asp Tyr Phe Asp Ala Arg
            100                 105                 110
```

```
Asn Tyr Leu Leu Pro Met Lys Asp Gln Leu Lys Asn Pro His Ala His
            115                 120                 125
His Asp Ala Cys Arg Thr Ile Leu Leu Asn Cys Leu Phe Phe Lys His
    130                 135                 140
Arg Asn Tyr Ile Thr Ser Asp Cys Val Pro Leu Val Ala Leu Cys Tyr
145                 150                 155                 160
Leu Arg Val Arg Gln Asn Phe Val Glu Ala Ile Met Thr Glu Ala Leu
                165                 170                 175
Arg Gly Glu Ile Asn Thr Lys Gly Ala Ala Ala Met Lys Lys Val
            180                 185                 190
Cys Glu Lys Ile Gly His Glu Ser Pro Asp Leu Leu His Leu Cys Phe
        195                 200                 205
Lys Thr Thr Val Leu Glu Lys Pro Lys Arg Ser Asn Lys Gln Tyr Ile
    210                 215                 220
Glu Asp Val Lys Ser Arg Ile Arg Thr Val Ser Thr Gly Asn Cys Arg
225                 230                 235                 240
Gln Val Leu Glu Glu Cys Tyr Phe Asn Val Leu Asp Tyr Pro Asp Ile
                245                 250                 255
Tyr Gln Ser Cys Arg Asn Phe Arg Arg Phe Cys Ser Glu Ile Gly Val
            260                 265                 270
Val Tyr Thr Pro Val Asp Ser Thr Phe Asp Leu Phe Gln Lys Pro Leu
        275                 280                 285
Ser Ala Glu Lys Leu Leu Ile Asp Thr Ser Ser Lys Ile Ser Glu Asp
    290                 295                 300
Leu Gly Leu Gly Phe Ser Lys Tyr Val Gln Lys Ser Ser Asn Leu
305                 310                 315                 320
Glu Ile Ala Ala Tyr Leu Val Asn Lys Thr Trp Val Tyr Asp Asn Asp
                325                 330                 335
Cys Arg Asn Lys Leu Lys Glu Leu Cys Leu His Ile Ala Ser Leu Pro
            340                 345                 350
Leu Thr Lys Gln Leu Cys Thr Leu Ala His Asp Arg Asn Ser Lys Leu
        355                 360                 365
Cys Arg Asp Phe Tyr Asn Ser Ile Gly Thr Glu Cys Tyr Ser Leu Tyr
    370                 375                 380
Tyr Glu Phe Lys Asn Val Gly Leu Leu Tyr Asn Tyr Thr Tyr Arg Leu
385                 390                 395                 400
Ser Arg Asp Gln Cys Ser Lys Tyr Val Glu Arg Cys Leu Phe Leu Arg
                405                 410                 415
Glu Gln Tyr Ala Tyr Trp Asn Ser Leu Asp Thr Cys Ala Asn Val Phe
            420                 425                 430
Ser Ser Cys Tyr Lys Glu Asp Met Asp Phe Ser Ala Lys Leu Asp Leu
        435                 440                 445
Leu Asn Arg Ile Lys Asp Lys Ile Val Val Pro Lys Gly Asn Thr Arg
    450                 455                 460
Tyr Phe Val Glu Leu Leu Cys Lys Ser Tyr Ile Val Ala Glu Cys Ser
465                 470                 475                 480
Ala Ser Asp Leu Met Phe Lys Ser Tyr Ala Leu Met Glu Ala Cys Leu
                485                 490                 495
His Pro Glu Arg Ile Cys Arg Glu Leu Lys Asn His Phe Ser Glu Glu
            500                 505                 510
Ser Arg Lys Leu Glu Asn Lys Leu Arg Ser Ile Leu Lys Pro Thr Tyr
        515                 520                 525
```

```
Tyr Glu Cys Lys Asp Leu Gly Gln Lys Cys Asn Ser Gly Phe Tyr Phe
            530                 535                 540

Asp Gly Asp Ile Glu Ala Gln Cys Asn His Phe Lys Lys Arg Cys Gln
545                 550                 555                 560

Asp Lys Gln Glu Arg Leu Lys Leu Ile Asn His Ile Val Asp Ser Ser
                565                 570                 575

Ala Leu Tyr Leu Ala Asn Glu Val Gln Cys Arg Thr Tyr Phe Asp Ser
            580                 585                 590

Phe Cys Gly Ala Asn Val Lys Gln Glu Phe Lys Gln Ile Cys Asn Lys
        595                 600                 605

Gly Ala Asn Gly Ile Cys Pro Asp Ile Ile Asp Ser Lys Glu His
    610                 615                 620

Cys Ala His Leu Ile Asn His Leu Thr Ser Leu Gly Ile Ser Ser Ser
625                 630                 635                 640

Ser Ala Ser Leu Pro Leu Asp Tyr Cys Asp Ser Ala Ile Asn Tyr Cys
                645                 650                 655

Asn Ser Leu Ser Lys Phe Cys Thr Glu Ser Lys Arg Gln Cys Asp Ser
            660                 665                 670

Val Ile Ser Phe Cys Thr Ser Glu Ser Lys Lys Thr Asp Glu Tyr Gly
        675                 680                 685

Ser Phe Ile Asp Gln Tyr Pro Ala Ala Ala Asn Ala Thr Lys Cys
    690                 695                 700

Lys Val Thr Leu Lys Glu Leu Cys Gln Asp Ser Ser Lys Lys Asp Ser
705                 710                 715                 720

Tyr Ser Thr Leu Cys Ala Tyr Asn Lys Asp Gly Tyr Thr Glu Ile Cys
                725                 730                 735

Lys Asn Leu Arg Asn Phe Ile Glu Lys Ala Cys Glu Asn Leu Arg Ile
            740                 745                 750

His Leu His Thr Tyr Asp Thr Asn Ser Leu Asn Thr Asn Lys Gly Ser
        755                 760                 765

Ala Gln Asp Arg Cys Thr Tyr Ile Arg Asn Leu Tyr Phe Lys Phe Lys
    770                 775                 780

Asn Ile Cys Leu Leu Val Asp Pro Phe Tyr Asp Leu Ser Pro Ile Ile
785                 790                 795                 800

Thr Gln Glu Cys Lys Thr Asn Ile Ser Glu Pro Ala Leu Pro Asp Lys
                805                 810                 815

Asp Pro Gln Pro Thr Ser Ser Pro Gln Pro Lys Pro Arg Pro Arg Pro
            820                 825                 830

Arg Pro Gln Pro Gln Pro His Pro His Pro Lys Pro Gln Pro Gln Pro
        835                 840                 845

Thr Pro Glu Pro Gln Pro Ala Pro Glu Pro Arg Pro Gln Pro
    850                 855                 860

Thr Ser Lys Pro Arg Pro Gln Pro Thr Ser Lys Pro Arg Pro Gln Pro
865                 870                 875                 880

Thr Pro Glu Pro Arg Pro Leu Pro Val Pro Gly Pro Leu Pro
                885                 890                 895

Val Pro Gly Pro Arg Pro Gln Pro Gln Pro Gln Pro Gln Pro
            900                 905                 910

Gln Pro Gln Pro Gln Pro Gln Pro Gln Pro Gln Pro Gln Pro
        915                 920                 925

Gln Pro Gln Pro Gln Pro Gln Pro Lys Pro Gln Pro Pro Ser Gln Ser
930                 935                 940
```

```
Thr Ser Glu Ser Ala Ser Gln Ser Lys Pro Lys Pro Thr Gln Thr
945                 950                 955                 960

Lys Pro Ser Pro Arg Pro His Pro Lys Pro Val Pro Lys Pro Ser Ser
                965                 970                 975

Ile Asp Thr Gly Pro Ser Lys Ser Asp Ser Ser Phe Ile Phe Thr Val
                980                 985                 990

Thr Lys Thr Ile Thr Lys Ile Ser Glu Thr Glu Lys Pro Ser Thr Lys
        995                1000                1005

Pro Ser Val Lys Pro Thr Ser Thr Lys Thr Thr Ser Lys Pro Ser
        1010                1015                1020

Thr Lys Pro Ser Thr Lys Pro Ser Val Lys Pro Ala Asn His Ser
        1025                1030                1035

Thr Lys Thr Thr Ser Glu Ser Glu Lys Pro Thr Leu Glu Glu Val
        1040                1045                1050

Pro Glu Thr Lys Gly Asn Gly Val Arg Val Ile Gly Phe Glu Gly
        1055                1060                1065

Leu Gln Leu Leu Ser Met Ile Val Ala Ile Ile Gly Ile Trp
        1070                1075                1080

Ile Met
    1085

<210> SEQ ID NO 5
<211> LENGTH: 3300
<212> TYPE: DNA
<213> ORGANISM: artificial
<220> FEATURE:
<223> OTHER INFORMATION: Nucleic acid molecule encoding the full-length
      mouse-derived Pneumocystis A12 protein

<400> SEQUENCE: 5 atgttttct taagaatcat ctttatattt attttttaa aaatatcata tgcagaaaac     60
acagataaac tctcagattt cgaaaaaaaa tatccagaat tatatcaagc aaatccacat    120
gctttaaaac tggaagcatt gaaaagcgga ttttcaggca atctgtaaa aaaaggattg    180 ggtgttttc atatagggaa tcttggtcat tatagagatc ataaaccagt tatattgcat    240
gtaattatgg gattaactgt tggactcgca gagtgtcgcg ggacactcgc cgaaagatgt    300
aaagtcataa aagccctagg aaatccaata acacaatatt gcaataaacc atatgataca    360
tgccaagatt attttgacgc tcgaaattac ttactcccta tgaaagatca attaaaaaac    420
ccacacgccc atcatgatgc atgcagaacg attttgctaa attgcctctt ttttaaacat    480
cgtaattata ttacttccga ttgtgttcct ttggtagcat tatgttattt gcgggttcgt    540
caaaactttg tagaagcaat tatgaccgaa gcattaagag gggaaattaa tactaagggt    600
gctgctgcag caatgaaaaa agtatgtgaa aaaattggac atgagagtcc ggacttgctt    660
catttatgtt ttaagaccac tgtattagaa aaacctaaaa ggtctaataa acagtatatt    720
gaagatgtta agtcaagaat aaggacagtt tcgactggaa attgccgtca ggttttggaa    780
gaatgctatt ttaatgttct agattatcca gatatttatc aatcatgtag gaattttcga    840
cgattctgtt cagaaatagg agttgtatat actccagtcg attccacttt tgatttattt    900
cagaagcccc tttctgcaga aagttactta attgatactt cttcaaaaat ctcagaagac    960
ttaggtcttg gtttttctaa atatgtacaa aaaaaatcaa gcaatcttga gattgcggca   1020
tatttagtta ataagacttg ggtctatgat aatgattgca gaaataaatt aaaagaacta   1080
tgtctgcata ttgcttctct accgcttaca aaacaactat gcacattagc acatgataga   1140
```

```
aattcgaaac tctgtaggga ttttttataac tctattggga ctgaatgcta ttctttatat   1200
tatgaattta agaatgttgg attattatac aattatactt atcgtctttc aagagatcaa   1260
tgctctaaat atgtagaaag atgtctttt cttagggagc aatatgctta ttggaattct   1320
ctagatactt gtgctaatgt attttcttca tgttataaag aagatatgga ttttcagcc   1380 aaattagatc ttctaaatag gataaaagat aagattgtag ttccaaaagg aaacacgagg   1440
tattttgtag agttattgtg taaaagctat attgtcgccg aatgcagcgc cagtgattta   1500
atgttcaaat cttatgctct tatggaagcc tgtcttcacc cagaaaggat ctgtagagaa   1560
ttaaaaaatc atttttccga agaatctagg aaattagaaa ataaattaag gagtatttta   1620
aaacccacat attatgaatg caaagatcta ggacaaaagt gcaactctgg attttatttt   1680
gatggagata tagaagctca atgcaatcat ttcaaaaaaa gatgtcaaga taaacaagag   1740
agactaaaat taattaatca tattgttgat tcatctgctc tttatctcgc aaatgaagta   1800
caatgcagaa cttatttcga cagtttttgt ggtgcgaatg taaaacaaga attcaaacaa   1860
atatgcaaca aaggagctaa tggcatatgc cctgatataa tagatgattc taaagaacat   1920
tgtgctcatt tgattaatca tttaacatct cttggaattt catcgtcttc tgcttcactt   1980
ccattggact attgcgactc agcgattaat tactgtaatt ctctttcgaa gttttgcacg   2040
gaatcaaaac gacagtgcga ttctgttatt tctttctgca ctagcgaatc aaaaaaaact   2100
gatgaatatg gttcttttat tgaccaatat cccgcggctg cagcaaatgc aaccaaatgc   2160
aaggtaactt tgaaagagtt atgccaagat tcaagcaaaa aagactctta ttcaacacta   2220
tgtgcttata ataaagatgg ttataccgaa atatgtaaaa acttaagaaa tttcatagaa   2280
aaagcatgcg agaatttgag aattcattta catacttatg atacaaactc actcaatacg   2340
aataaaggat ctgctcaaga tagatgcact tatataagaa atctttactt taaatttaaa   2400
aatatatgtt tattggttga tcctttctat gacttatctc ctattatcac tcaagaatgt   2460
aaaaccaata tatccgaacc agcactgcct gataaggatc tcaacctac atcttcacct   2520 cagccaaaac ctcggccaag acctcgacct caacctcaac ctcatccaca tccaaaacct   2580
cagcctcagc cgacgccaga acctcagcct cagccggcgc cagaacctcg acctcagccg   2640
acgtcaaaac ctcgacctca gccaacgtca aaacctcgac ctcagccgac gccagaacct   2700
cgacctctgc cggtgccagg acctggacct ctgccggtgc caggacctcg acctcaacct   2760
caacctcaac ctcaacctca gcctcaacct caacctcagc tcaacctcca acctcagcct   2820
cagcctcagc ctcagcctca gcctcaacct cagccgaagc ctcaaccacc atctcagtca   2880
acatcagaat cagcatcgca atccaaacca aaaccaacaa cacaaacaaa accgtcaccg   2940
agaccacacc caaagccggt gccaaaacca tcatcgatag acacaggacc atcaaaatcg   3000
gattcaagct tcattttttac agtaacaaaa acaataacaa agatatcaga aacagaaaaa   3060
ccatctacaa aacctctgt gaaaccaacc tctacaaaga caacatcaaa accatctaca   3120
aaaccatcta caaaccatc tgtaaaacca gcctctacaa agacaacatc agaatcagaa   3180
aaaccaacat ggaagaagt tccagaaact aaagggaatg gtgtaagagt aataggattt   3240 gagggggtttac aattattatc aatgattgtt gcaataataa ttgggatatg gataatgtaa   3300
```

<210> SEQ ID NO 6
<211> LENGTH: 66
<212> TYPE: PRT
<213> ORGANISM: artificial
<220> FEATURE:
<223> OTHER INFORMATION: Human-derived Pneumocystis A12 protein fragment -continued

<400> SEQUENCE: 6

Leu Leu Cys Ser Met Glu Val Val Phe Lys Lys Asp His Ser Glu His
1               5                   10                  15

Lys Tyr Val Glu Lys Lys Glu Thr Glu Ala Ala Asn Pro Leu Lys Ala
            20                  25                  30

Gln Ala Trp Lys Ser Gln Asp Val Pro Ala Thr Ile Ser Tyr Trp Ser
        35                  40                  45

Lys Gln Ser Gln Gly Gln Pro Arg Glu Gly Val Asp Met Phe His Leu
    50                  55                  60

Leu Met
65

<210> SEQ ID NO 7
<211> LENGTH: 24
<212> TYPE: DNA
<213> ORGANISM: artificial
<220> FEATURE:
<223> OTHER INFORMATION: 2SR2 Reverse primer

<400> SEQUENCE: 7
atcttctttg tagcatggaa gttg                                           24

<210> SEQ ID NO 8
<211> LENGTH: 21
<212> TYPE: DNA
<213> ORGANISM: artificial
<220> FEATURE:
<223> OTHER INFORMATION: 2SF3 Forward primer

<400> SEQUENCE: 8
gtggcctatg gcaacttcca g                                              21

<210> SEQ ID NO 9
<211> LENGTH: 15
<212> TYPE: DNA
<213> ORGANISM: artificial
<220> FEATURE:
<223> OTHER INFORMATION: SKYVE Forward primer

<400> SEQUENCE: 9
ctaaatatgt agaaa                                                     15

<210> SEQ ID NO 10
<211> LENGTH: 15
<212> TYPE: DNA
<213> ORGANISM: artificial
<220> FEATURE:
<223> OTHER INFORMATION: SKYVE Reverse primer

<400> SEQUENCE: 10
tttctacata tttag                                                     15

<210> SEQ ID NO 11
<211> LENGTH: 113
<212> TYPE: PRT
<213> ORGANISM: artificial
<220> FEATURE:
<223> OTHER INFORMATION: A12 Protein Region

```
<400> SEQUENCE: 11

Lys Thr Trp Val Tyr Asp Asn Asp Cys Arg Asn Lys Leu Lys Glu Leu
1               5                   10                  15

Cys Leu His Ile Ala Ser Leu Pro Leu Thr Lys Gln Leu Cys Thr Leu
            20                  25                  30

Ala His Asp Arg Asn Ser Lys Leu Cys Arg Asp Phe Tyr Asn Ser Ile
        35                  40                  45

Gly Thr Glu Cys Tyr Ser Leu Tyr Tyr Glu Phe Lys Asn Val Gly Leu
    50                  55                  60

Leu Tyr Asn Tyr Thr Tyr Arg Leu Ser Arg Asp Gln Cys Ser Lys Tyr
65                  70                  75                  80

Val Glu Arg Cys Leu Phe Leu Arg Glu Gln Tyr Ala Tyr Trp Asn Ser
                85                  90                  95

Leu Asp Thr Cys Ala Asn Val Phe Ser Ser Cys Tyr Lys Glu Asp Met
            100                 105                 110

Asp

<210> SEQ ID NO 12
<211> LENGTH: 66
<212> TYPE: PRT
<213> ORGANISM: artificial
<220> FEATURE:
<223> OTHER INFORMATION: Clone 2 Infected Human (3'-5' direction)

<400> SEQUENCE: 12

Leu Leu Cys Ser Met Glu Val Val Phe Lys Lys Asp His Ser Glu His
1               5                   10                  15

Lys Tyr Val Glu Lys Lys Glu Thr Glu Ala Ala Asn Pro Leu Lys Ala
            20                  25                  30

Gln Ala Trp Lys Ser Gln Asp Val Pro Ala Thr Ile Ser Tyr Trp Ser
        35                  40                  45

Lys Gln Ser Gln Gly Gln Pro Arg Glu Gly Val Asp Met Phe His Leu
    50                  55                  60

Leu Met
65

<210> SEQ ID NO 13
<211> LENGTH: 64
<212> TYPE: PRT
<213> ORGANISM: artificial
<220> FEATURE:
<223> OTHER INFORMATION: Clone 3 Infected Human (3'-5' direction)
<220> FEATURE:
<221> NAME/KEY: misc_feature
<222> LOCATION: (61)..(61)
<223> OTHER INFORMATION: Xaa can be any naturally occurring amino acid

<400> SEQUENCE: 13

Cys Ser Met Glu Val Val Phe Lys Lys Asp His Ser Glu His Lys Tyr
1               5                   10                  15

Val Glu Lys Lys Glu Thr Glu Ala Ala Asn Pro Leu Lys Ala Gln Ala
            20                  25                  30

Trp Lys Ser Gln Asp Val Pro Ala Thr Ile Ser Tyr Trp Ser Lys Gln
        35                  40                  45

Ser Gln Gly Gln Pro Arg Glu Gly Val Asp Met Phe Xaa Leu Leu Met
    50                  55                  60
```